US012595250B2

(12) United States Patent
Hecht et al.

(10) Patent No.: US 12,595,250 B2
(45) Date of Patent: Apr. 7, 2026

(54) SUBSTITUTED PYRIMIDINE COMPOUNDS AS MULTIFUNCTIONAL RADICAL QUENCHERS AND THEIR USES

(71) Applicant: ARIZONA BOARD OF REGENTS ON BEHALF OF ARIZONA STATE UNIVERSITY, Scottsdale, AZ (US)

(72) Inventors: Sidney Hecht, Phoenix, AZ (US); Omar Khdour, Phoenix, AZ (US); Arnaud Chevalier, Bruere Allichamps (FR)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 919 days.

(21) Appl. No.: 17/841,288

(22) Filed: Jun. 15, 2022

(65) Prior Publication Data

US 2022/0324841 A1 Oct. 13, 2022

Related U.S. Application Data

(62) Division of application No. 16/327,287, filed as application No. PCT/US2017/047640 on Aug. 18, 2017, now Pat. No. 11,390,605.

(60) Provisional application No. 62/379,658, filed on Aug. 25, 2016.

(51) Int. Cl.

| | |
|---|---|
| ***C07D 403/04*** | (2006.01) |
| ***A61K 31/506*** | (2006.01) |
| ***A61P 39/06*** | (2006.01) |
| ***C07D 239/60*** | (2006.01) |
| ***C07D 403/14*** | (2006.01) |

(52) U.S. Cl.

CPC .......... *C07D 403/04* (2013.01); *A61K 31/506* (2013.01); *A61P 39/06* (2018.01); *C07D 239/60* (2013.01); *C07D 403/14* (2013.01)

(58) Field of Classification Search

CPC .................. A61P 39/06; C07D 243/04; A61K 31/505–506; C07F 243/04; C07F 403/04–14

See application file for complete search history.

(56) References Cited

U.S. PATENT DOCUMENTS

| | | | | |
|---|---|---|---|---|
| 8,952,025 B2 * | 2/2015 | Hecht | .................. | C07D 403/04 544/320 |
| 10,364,227 B2 * | 7/2019 | Hecht | .................. | C07D 239/47 |
| 2013/0267546 A1 * | 10/2013 | Hecht | .................. | C07D 239/42 544/320 |

FOREIGN PATENT DOCUMENTS

WO WO-2016133959 A1 * 8/2016 .............. A61P 25/00

OTHER PUBLICATIONS

Khdour et al., "An optimized pyrimidinol multifunctional radical quencher," ACS Med. Chem. Lett. 2013;4(8):724-29. PMID: 24900738. (Year: 2013).*

Mastroeni et al., "Novel antioxidants protect mitochondria from the effects of oligomeric amyloid beta and contribute to the maintenance of epigenome function," ACS Chem. Neurosci. 2015;6(4):588-98. PMID: 25668062. (Year: 2015).*

Chevalier et al., "Optimization of pyrimidinol antioxidants as mitochondrial protective agents: ATP production and metabolic stability," Bioorg. Med. Chem. 2016;24(21):5206-20. PMID: 27624526. (Year: 2016).*

* cited by examiner

*Primary Examiner* — Theodore R. Howell

(74) *Attorney, Agent, or Firm* — Viksnins Harris Padys Malen LLP

(57) ABSTRACT

The invention provides compounds having the general formula I:

I

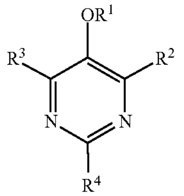

and pharmaceutically acceptable salts thereof, wherein the variables $R^1$, $R^2$, $R^3$ and $R^4$ have the meaning as described herein, and compositions containing such compounds and methods for using such compounds and compositions.

15 Claims, 5 Drawing Sheets

1a

1b

1c

2a

2b

2c

3a

3b

3c

4a

4b and

4c

SUBSTITUTED PYRIMIDINE COMPOUNDS AS MULTIFUNCTIONAL RADICAL QUENCHERS AND THEIR USES

RELATED APPLICATIONS

This application is a divisional of U.S. patent application Ser. No. 16/327,287, filed Feb. 21, 2019, which is a 35 U.S.C. § 371 application of International Application Serial No. PCT/US2017/047640, filed Aug. 18, 2017; which claims the benefit of U.S. Provisional Application Ser. No. 62/379,658, filed Aug. 25, 2016. The entire content of the applications referenced above are hereby incorporated by reference herein.

BACKGROUND OF THE INVENTION

The critical function of mitochondria in eukaryotic cells is now well defined (Henze, K., et al. *Nature* 2003, 426, 127; Saraste, M. W. *Science* 1999, 283, 1488; McBride, H. M., et al. *Curr. Biol.* 2006, 16, R551; Newmeyer, D. D., et al. *Cell* 2003, 112, 481; Graier, W. F. *Eur. J. Physiol.* 2007, 455, 375; Bras, M., et al. *Biochemistry* (Moscow) 2005, 70, 231; and Fiore, C., et al. *Biochimie* 1998, 80, 13). Their essential role in energy metabolism through the production of adenosine-5'-triphosphate (ATP) is one of the main points which can affect the fate of cells (Saraste, M. W. *Science* 1999, 283, 1488; and McBride, H. M., et al. *Curr. Biol.* 2006, 16, R551). This ATP production is the result of conversion of ADP in mitochondrial complex V. This process involves protons transported from the inner mitochondrial membrane to the intermembrane space which is coupled with an electron flow through mitochondrial complexes I-IV. This process is called oxidative phosphorylation (OXPHOS). The decline in mitochondrial function is connected to aging, neurodegenerative diseases and many complex mitochondrial diseases (Markesbery, W. R., et al. *Brain Pathol.* 1999, 9, 133; Calabrese, V., et al. *Neurol. Sci.* 2005, 233, 145; Lin, M. T., et al. *Nature* 2006, 443, 787; DiMauro, S., et al. *Annu. Rev. Neurosci.* 2008, 31, 91; and Armstrong, J. S., et al. *FASEB J.* 2010, 24, 2152). Currently there is a need for new compounds that protect mitochondrial function.

SUMMARY OF THE INVENTION

The invention provides compounds that protect the mitochondrial function. Accordingly, the invention provides a compound of formula I.

formula I

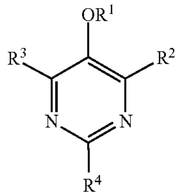

wherein $R^1$ is hydrogen or $C_{1-6}$ alkyl;

$R^2$ is $C_{1-20}$ alkyl, $C_{2-20}$ alkenyl or $C_{2-20}$ alkynyl, wherein the $C_{1-20}$ alkyl, $C_{2-20}$ alkenyl and $C_{2-20}$ alkynyl are optionally substituted with one or more groups independently selected from —F, —Cl, —Br, —I, —$OR^a$, —$SR^a$, —$N(R^a)_2$, oxo, —$NO_2$ and —CN;

$R^3$ is —$OR^5$ or —$NR^6R^7$;

$R^4$ is —$OR^8$ or —$NR^9R^{10}$;

$R^5$ is $C_{3-10}$ cycloalkyl or $C_{1-8}$ alkyl; wherein $C_{3-10}$ cycloalkyl and $C_{1-8}$ alkyl are optionally substituted with one or more groups independently selected from $C_{1-4}$ alkyl, $C_{1-4}$ haloalkyl, —F, —Cl, —Br, —I, —$OR^b$, —$SR^b$, —$N(R^b)_2$, oxo, —$NO_2$ and —CN;

$R^6$ is $C_{1-6}$ alkyl, $C_{2-6}$ alkenyl or $C_{2-6}$ alkynyl, and wherein the $C_{1-6}$ alkyl, $C_{2-6}$ alkenyl and $C_{2-6}$ alkynyl are optionally substituted with one or more groups independently selected from —F, —Cl, —Br, —I, —$OR^c$, —$SR^c$, —$N(R^c)_2$, oxo, —$NO_2$ and —CN; $R^7$ is $C_{1-6}$ alkyl, $C_{2-6}$ alkenyl or $C_{2-6}$ alkynyl, and wherein the $C_{1-6}$ alkyl, $C_{2-6}$ alkenyl and $C_{2-6}$ alkynyl are optionally substituted with one or more groups independently selected from —F, —Cl, —Br, —I, —$OR^d$, —$SR^d$, —$N(R^d)_2$, oxo, —$NO_2$ and —CN; or $R^6$ and $R^7$ taken together with the nitrogen to which they are attached form a 3-10 membered heterocycle that is optionally substituted with one or more groups independently selected from $C_{1-4}$ alkyl, $C_{1-4}$ haloalkyl, —F, —Cl, —Br, —I, —$OR^e$, —$SR^e$, —$N(R^e)_2$, oxo, —$NO_2$ and —CN;

$R^8$ is $C_{3-10}$ cycloalkyl or $C_{1-8}$ alkyl; wherein $C_{3-10}$ cycloalkyl and $C_{1-8}$ alkyl are optionally substituted with one or more groups independently selected from $C_{1-4}$ alkyl, $C_{1-4}$ haloalkyl, —F, —Cl, —Br, —I, —$OR^e$, —SR, —$N(R)_2$, oxo, —$NO_2$ and —CN;

$R^9$ is $C_{1-6}$ alkyl, $C_{2-6}$ alkenyl or $C_{2-6}$ alkynyl, and wherein the $C_{1-6}$ alkyl, $C_{2-6}$ alkenyl and $C_{2-6}$ alkynyl are optionally substituted with one or more groups independently selected from —F, —Cl, —Br, —I, —$OR^g$, —$SR^g$, —$N(R^g)_2$, oxo, —$NO_2$ and —CN; $R^{10}$ is $C_{1-6}$ alkyl, $C_{2-6}$ alkenyl or $C_{2-6}$ alkynyl, and wherein the $C_{1-6}$ alkyl, $C_{2-6}$ alkenyl and $C_{2-6}$ alkynyl are optionally substituted with one or more groups independently selected from —F, —Cl, —Br, —I, —$OR^h$, —$SR^h$, —$N(R^h)_2$, oxo, —$NO_2$ and —CN; or $R^9$ and $R^{10}$ taken together with the nitrogen to which they are attached form a 3-10 membered heterocycle that is optionally substituted with one or more groups independently selected from $C_{1-4}$ alkyl, $C_{1-4}$ haloalkyl, —F, —Cl, —Br, —I, —$OR^i$, —$SR^i$, —$N(R^i)_2$, oxo, —$NO_2$ and —CN;

each $R^a$ is independently hydrogen or $C_{1-4}$ alkyl; or two $R^a$ taken together with the nitrogen to which they are attached form pyrrolidinyl, piperidinyl, piperazinyl or morpholinyl;

each $R^b$ is independently hydrogen or $C_{1-4}$ alkyl; or two $R^b$ taken together with the nitrogen to which they are attached form pyrrolidinyl, piperidinyl, piperazinyl or morpholinyl;

each $R^c$ is independently hydrogen or $C_{1-4}$ alkyl; or two $R^c$ taken together with the nitrogen to which they are attached form pyrrolidinyl, piperidinyl, piperazinyl or morpholinyl;

each $R^d$ is independently hydrogen or $C_{1-4}$ alkyl; or two $R^d$ taken together with the nitrogen to which they are attached form pyrrolidinyl, piperidinyl, piperazinyl or morpholinyl;

each $R^e$ is independently hydrogen or $C_{1-4}$ alkyl; or two $R^e$ taken together with the nitrogen to which they are attached form pyrrolidinyl, piperidinyl, piperazinyl or morpholinyl;

each $R^f$ is independently hydrogen or $C_{1-4}$ alkyl; or two $R^f$ taken together with the nitrogen to which they are attached form pyrrolidinyl, piperidinyl, piperazinyl or morpholinyl;

each $R^g$ is independently hydrogen or $C_{1-4}$ alkyl; or two $R^g$ taken together with the nitrogen to which they are attached form pyrrolidinyl, piperidinyl, piperazinyl or morpholinyl;

each $R^h$ is independently hydrogen or $C_{1-4}$ alkyl; or two $R^h$ taken together with the nitrogen to which they are attached form pyrrolidinyl, piperidinyl, piperazinyl or morpholinyl; and each $R^i$ is independently hydrogen or $C_{1-4}$ alkyl; or two $R^i$ taken together with the nitrogen to which they are attached form pyrrolidinyl, piperidinyl, piperazinyl or morpholinyl;

or a pharmaceutically acceptable salt thereof.

The invention also provides a pharmaceutical composition comprising a compound of formula I or a pharmaceutically acceptable salt thereof, and a pharmaceutically acceptable carrier.

The invention also provides a method for treating mitochondrial disease, neurodegenerative disease, cardiovascular disease, cancer or diabetes in an animal comprising administering a compound of formula I or a pharmaceutically acceptable salt thereof to the animal.

The invention also provides a compound of formula I or a pharmaceutically acceptable salt thereof for use in medical therapy.

The invention also provides a compound of formula I or a pharmaceutically acceptable salt thereof for the prophylactic or therapeutic treatment of mitochondrial disease, neurodegenerative disease, cardiovascular disease, cancer or diabetes.

The invention also provides the use of a compound of formula I or a pharmaceutically acceptable salt thereof to prepare a medicament for treating mitochondrial disease, neurodegenerative disease, cardiovascular disease, cancer or diabetes in an animal (e.g. a mammal such as a human).

The invention also provides processes and intermediates disclosed herein that are useful for preparing a compound of formula I or a salt thereof.

DETAILED DESCRIPTION

Figure 1:
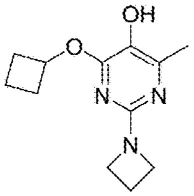
FIG. 1 illustrates the chemical structures of the representative compounds of formula I (compounds 1a-1c, 2a-2c, 3a-3c and 4a-4c).
Figure 1:
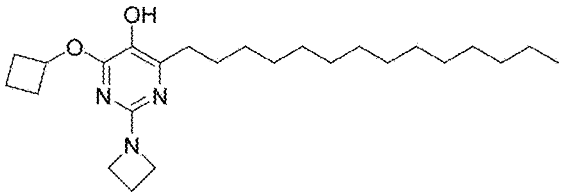
Figure 1:
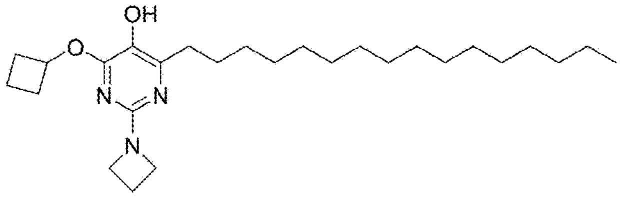
Figure 1:
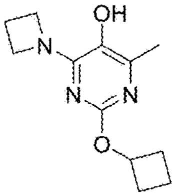
Figure 1:
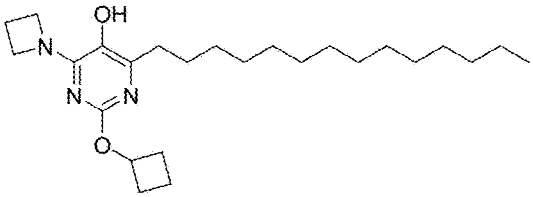
Figure 1:
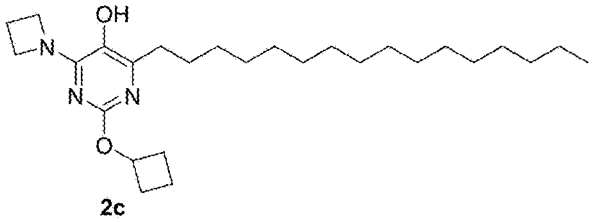
Figure 1:
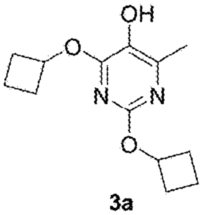
Figure 1:
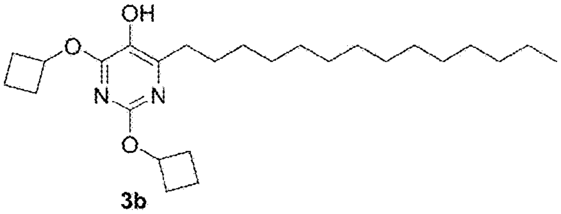
Figure 1:
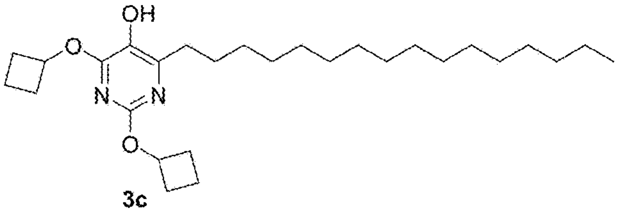
Figure 1:
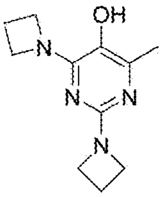
Figure 1:
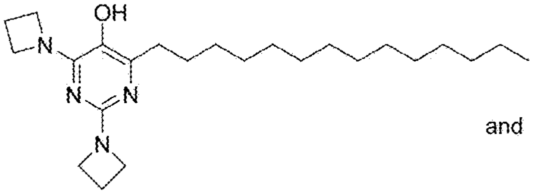
Figure 1:
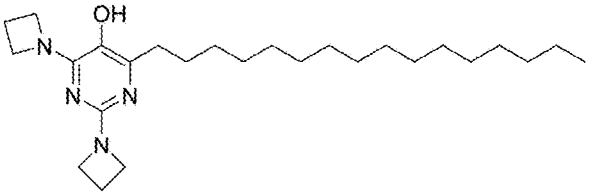

The term "alkyl", by itself or as part of another substituent, means, unless otherwise stated, a straight or branched chain hydrocarbon radical, having the number of carbon atoms designated (i.e., $C_{1-6}$ means one to six carbons). Non limiting examples of "alkyl" include methyl, ethyl, propyl, isopropyl, butyl, iso-butyl, sec-butyl, pentyl, 3-pentyl, hexyl and decyl.

The term "alkenyl" refers to an unsaturated alkyl radical having one or more double bonds. Non limiting examples of "alkenyl" include vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 2,4-pentadienyl. Similarly, the term "alkynyl" refers to an unsaturated alkyl radical having one or more triple bonds.

The term "haloalkyl" means an alkyl that is optionally substituted with one or more halo. Non limiting examples of "haloalkyl" include iodomethyl, bromomethyl, chloromethyl, fluoromethyl, trifluoromethyl, 2-chloroethyl, 2-fluoroethyl, 2,2,2-trifluoroethyl 2,2-difluoroethyl and pentafluoroethyl.

The term "cycloalkyl" refers to a saturated or a partially unsaturated all carbon ring having 3 to 10 carbon atoms. As used herein, "cycloalkyl" is also meant to refer to bicyclic, polycyclic and spirocyclic hydrocarbon ring system, such as, for example, bicyclo[2.2.1]heptane, pinane, bicyclo[2.2.2]octane, adamantane, norborene, spirocyclic C5-12 alkane, etc.

The term "heterocycle" refers to a saturated or partially unsaturated ring system radical having the overall having from 3-10 ring atoms that contain from one to five heteroatoms selected from N, O, and S. Unless otherwise stated, a "heterocycle" ring can be a monocyclic, a bicyclic, spirocyclic or a polycylic ring system. Non limiting examples of "heterocycle" rings include pyrrolidine, piperidine, N-methylpiperidine, imidazolidine, pyrazolidine, butyrolactam, valerolactam, imidazolidinone, hydantoin, dioxolane, phthalimide and piperidine.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

In one embodiment, $R^1$ is hydrogen.

In one embodiment, $R^2$ is $C_{1-20}$ alkyl.

In one embodiment, $R^2$ is $C_{10-20}$ alkyl.

In one embodiment, $R^2$ is methyl, tetradecyl or hexadecyl.

In one embodiment, $R^5$ is cyclobutyl.

In one embodiment, $R^6$ and $R^7$ taken together with the nitrogen to which they are attached form a 3-10 membered heterocycle that is optionally substituted with one or more groups independently selected from $C_{1-4}$ alkyl, $C_{1-4}$ haloalkyl, —F, —Cl, —Br, —I, —$OR^e$, —$SR^e$, —$N(R^e)_2$, oxo, —$NO_2$ and —CN.

In one embodiment, $R^6$ and $R^7$ taken together with the nitrogen to which they are attached form

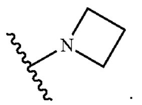 [SMILES: *N1CCC1]

In one embodiment, $R^9$ and $R^{10}$ taken together with the nitrogen to which they are attached form a 3-10 membered heterocycle that is optionally substituted with one or more groups independently selected from $C_{1-4}$ alkyl, $C_{1-4}$ haloalkyl, —F, —Cl, —Br, —I, —$OR^i$, —SR, —$N(R^i)_2$, oxo, —$NO_2$ and —CN.

In one embodiment, $R^9$ and $R^{10}$ taken together with the nitrogen to which they are attached form

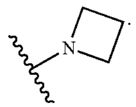 [SMILES: *N1CCC1]

In one embodiment, $R^3$ is —$OR^5$ and $R^4$ is —$NR^9R^{10}$ or $R^3$ is —$NR^6R^7$ and $R^4$ is —$OR^8$.

In one embodiment, the compound is a compound of formula Ia:

formula Ia

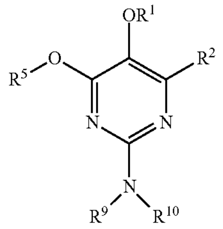

or a pharmaceutically acceptable salt thereof.

In one embodiment, $R^2$ in the compound of formula Ia is $C_{10-20}$ alkyl.

In one embodiment, $R^9$ and $R^{10}$ in the compound of formula Ia taken together with the nitrogen to which they are attached form a 3-10 membered heterocycle that is optionally substituted with one or more groups independently selected from $C_{1-4}$ alkyl, $C_{1-4}$ haloalkyl, —F, —Cl, —Br, —I, —$OR^i$, —$SR^i$, —$N(R^i)_2$, oxo, —$NO_2$ and —CN.

In one embodiment, the compound is a compound of formula Ib:

formula Ib

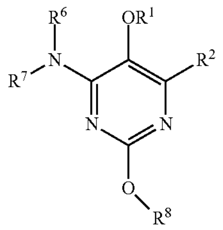

or a pharmaceutically acceptable salt thereof.

In one embodiment, $R^2$ in the compound of formula Ia is $C_{10-20}$ alkyl.

In one embodiment, $R^6$ and $R^7$ in the compound of formula Ia taken together with the nitrogen to which they are attached form a 3-10 membered heterocycle that is optionally substituted with one or more groups independently selected from $C_{1-4}$ alkyl, $C_{1-4}$ haloalkyl, —F, —Cl, —Br, —I, —$OR^i$, —$SR^i$, —$N(R^i)_2$, oxo, —$NO_2$ and —CN.

In one embodiment, $R^3$ is

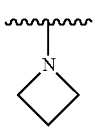
or
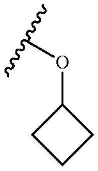
.

In one embodiment, $R^4$ is

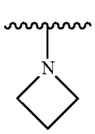
or
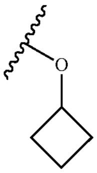
.

In one embodiment, the compound is selected from the group consisting of:

1a

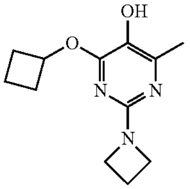

1b

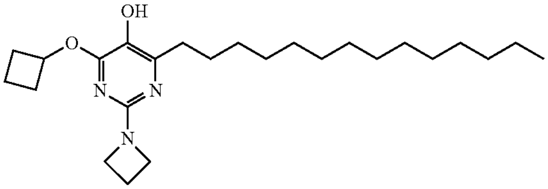

1c

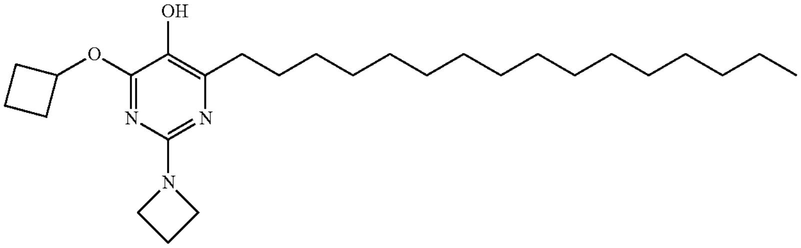

2a

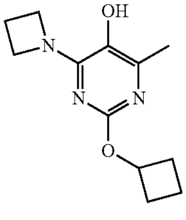

2b

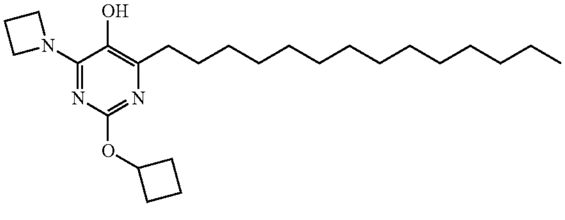

2c

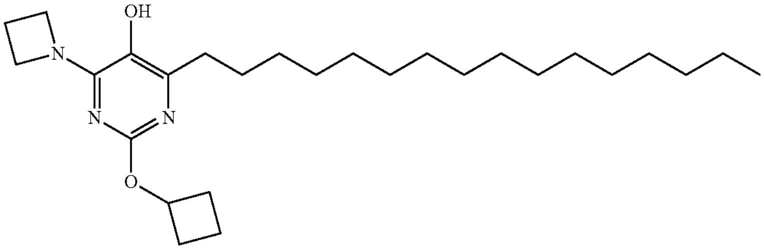

-continued

3a

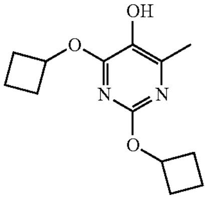

3b

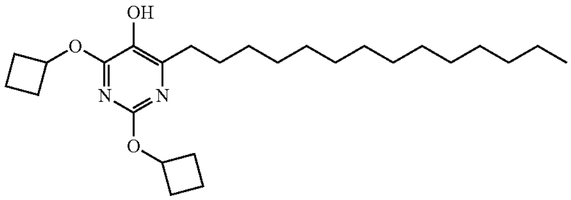

3c

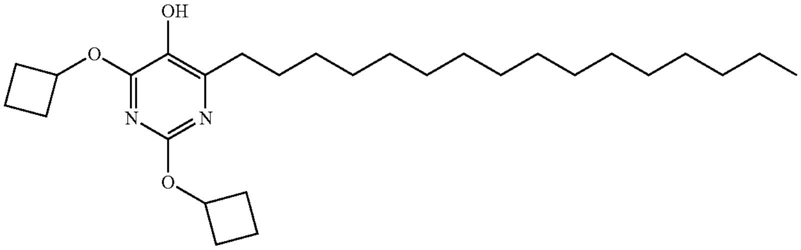

4a

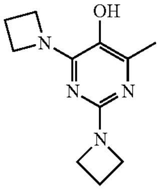

4b

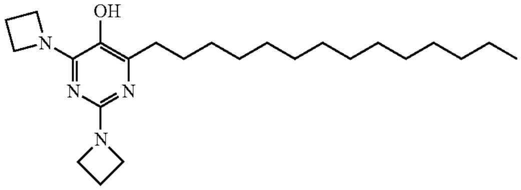

and

4c

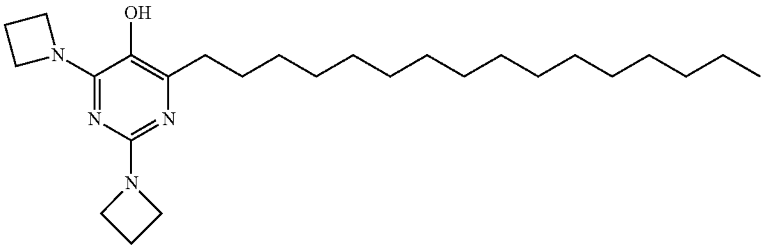

;

and pharmaceutically acceptable salts thereof.

In one embodiment, the neurodegenerative disease is amyotrophic lateral sclerosis (ALS), Alzheimer's disease (AD), Parkinson's disease (PD) or Friedreich's ataxia (FRDA).

In one embodiment, the invention provides a method of quenching lipid peroxidation and/or suppress reactive oxygen species (ROS) and/or preserving mitochondrial membrane potential and/or augmenting ATP production in an animal comprising administering to the animal an effective amount of compound of formula (I) or a pharmaceutically acceptable salt thereof.

In one embodiment, the invention also provides a method of quenching lipid peroxidation and/or suppress reactive oxygen species (ROS) and/or preserving mitochondrial membrane potential and/or augmenting ATP production in a cell in vitro comprising contacting the cell with an effective amount of compound of formula (I) or a pharmaceutically acceptable salt thereof.

In one embodiment, the invention provides a compound of formula (I) or a pharmaceutically acceptable salt thereof for use in quenching lipid peroxidation and/or suppress reactive oxygen species (ROS) and/or preserving mitochondrial membrane potential and/or augmenting ATP production.

In one embodiment, the invention provides the use of a compound of formula (I) or a pharmaceutically acceptable salt thereof for the manufacture of a medicament for quenching lipid peroxidation and/or suppress reactive oxygen species (ROS) and/or preserving mitochondrial membrane potential and/or augmenting ATP production.

Processes and intermediates useful for preparing compounds of formula I are provided as further embodiments of the invention and are illustrated by the following procedures in which the meanings of the generic radicals are as given above unless otherwise qualified.

Compounds of formula (I) may be prepared by the process illustrated in Schemes 1-3. Representative compounds of formula (I) are compounds 1a-c, 2a-c, 3a-c and 4a-c (FIG. 1).

The synthesis began with an aromatic nucleophilic substitution reaction of 2,4-dichloro-6-methylpyrimidine and cyclobutanol. Two regioisomers (5a and 5b) in an almost equimolar ratio were afforded, resulting respective yields of 35 and 34%. The use of the 2-(azetidin-1-yl)-4-cyclobutoxy-6-methylpyrimidine (5a) gave access to a first family of regioisomers. First by bromination or the pyrimidinol ring in position 5, the resulting aryl bromide 6 was hydroxylated via a sequence of boronylation-oxydation to obtain the redox core 1a of this family of regioisomers. An alkylation beforehand of the compound 5a to incorporate the 14 and 16 carbons side chains led to the compounds 7a and 7b with respectively 76 and 84% yields. The bromination followed by the hydroxylation step gave the quenchers 1b and 1c to complete a set of 3 quenchers for a first regioisomer family structurally similar to the MRQ previously reported by our team. The same sequence was applied to the compound 5b and the preparation of 3 new analogues was achieved as the results of what the Redox core 2a and the 14 and 16 carbons analogues 2b and 2b were obtained with respectively 55, 56 and 56% overall yields starting from the compound 5b. This completed a set of 6 quenchers in which the two isomers of alkoxy-aminyl pyrimidinols were presented in 3 different forms (1, 14 and 16 carbons).

Scheme 1. Synthesis of compounds 1a-c and 2a-c

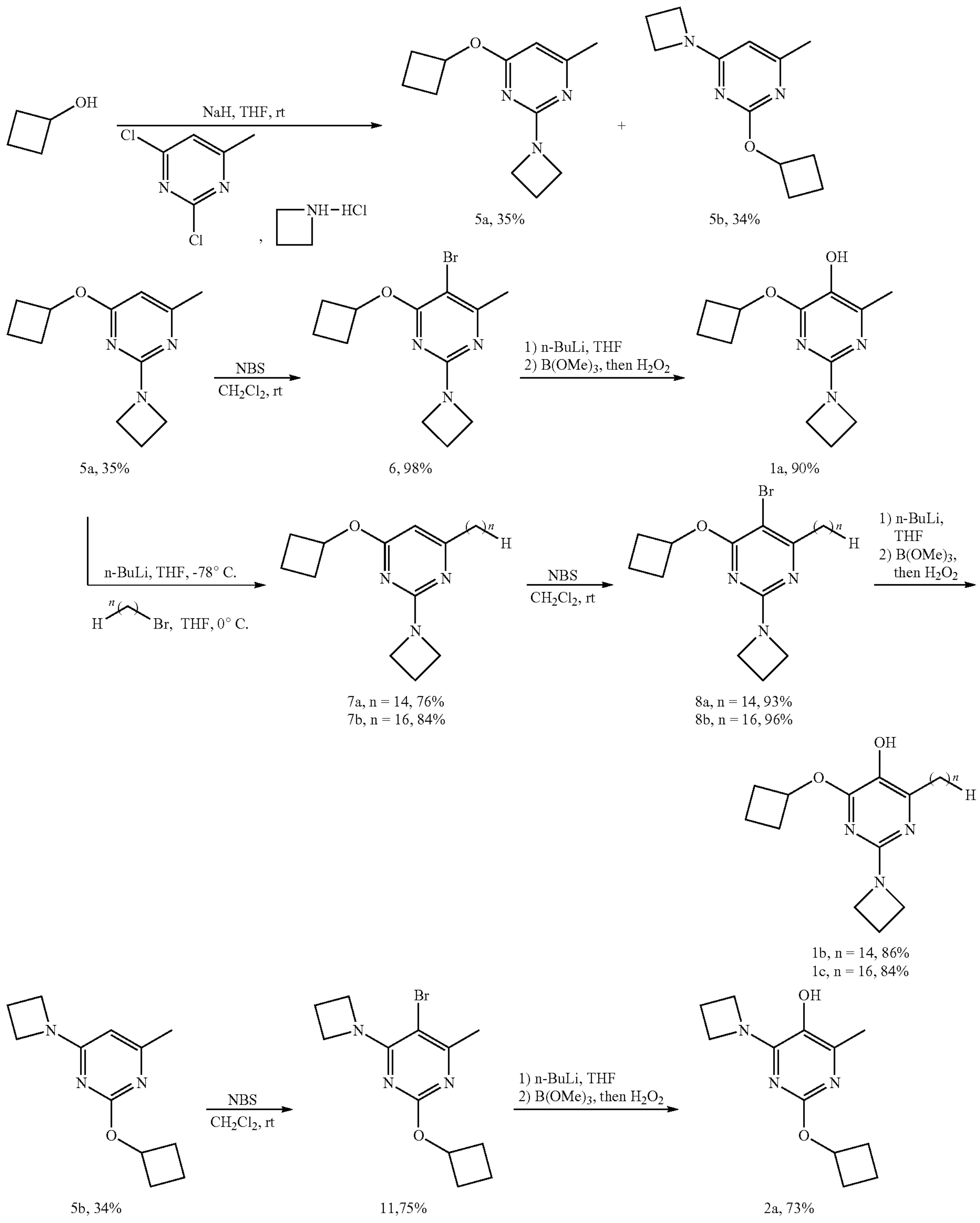

-continued

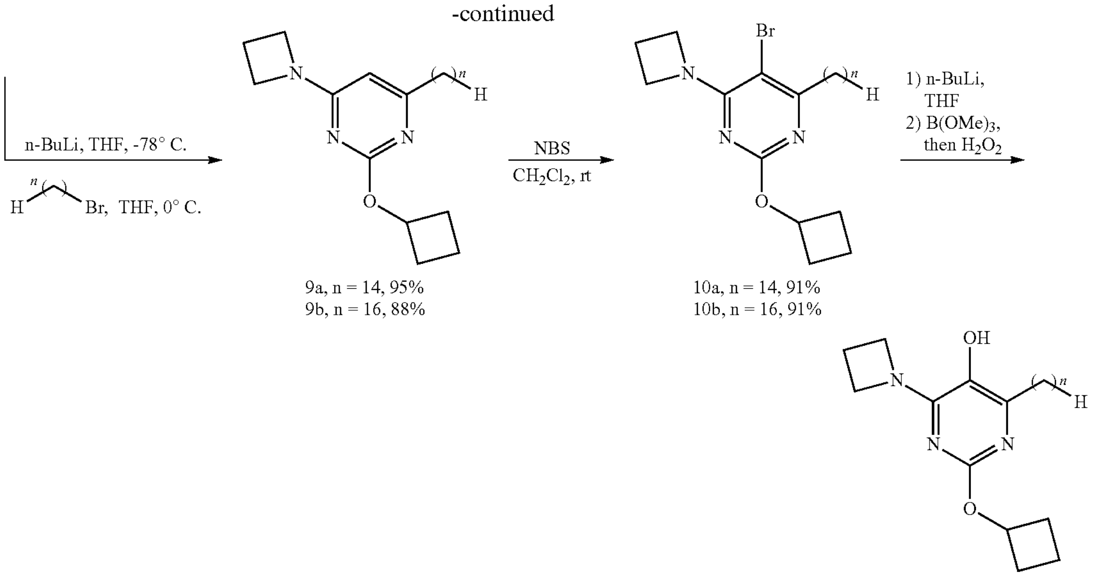

9a, n = 14, 95%
9b, n = 16, 88%

10a, n = 14, 91%
10b, n = 16, 91%

2b, n = 14, 68%
2c, n = 16, 70%

In Scheme 2, the use of an excess of cyclobutanol during the first step enabled the synthesis of the di-cyclobutoxy-6-methylpyrimidine (12) in 91% yield which has been used for the preparation of three new compounds following the same synthetic strategy. Redox core 3a was then obtained in 58% overall yield starting from the 2,4-dichloro-6-methylpyrimidine. After alkylation of the compound 12 followed by the bromination and hydroxylation steps, the 14 and 16 carbon analogues of the di-alkoxypyrimidinol family (3b and 3c) were obtained in 33 and 41% overall yields, respectively.

Scheme 2. Synthesis of compounds 3a-c

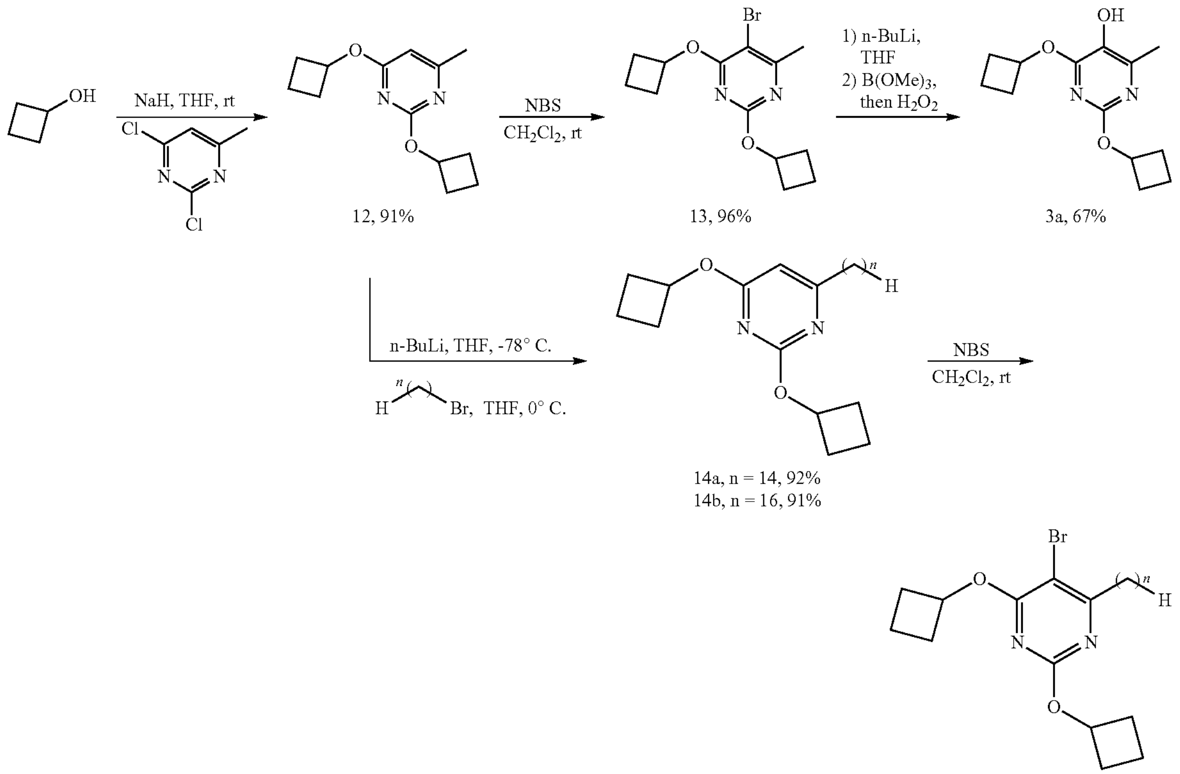

12, 91%

13, 96%

3a, 67%

14a, n = 14, 92%
14b, n = 16, 91%

15a, n = 14, 87%
15b, n = 16, 96%

-continued

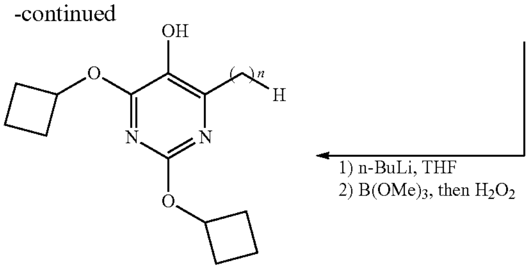

3b, n = 14, 46%
3c, n = 16, 52%

In Scheme 3, the preparation of the (2,4)-di-azetidinyl-6-methylpyrimidine (16) was achieved using a copper catalyzed nucleophilic substitution of both chlorine atoms of the 2,4-dichloro-6-methylpyrimidine with an excess of azetidine. The resulting compound 16, isolated in 78% yield, was then brominated to obtain the arylbromide 17 which was hydroxylated to obtain the redox core 4a in 66% yield. The 14 and 16 carbon analogues of 4a were prepared using the previously described sequence of alkylation, bromination and hydroxylation. The quenchers 4b and 4c were then recovered in 40 and 38% overall yields, respectively, starting from 2,4-dichloro-6-methylpyrimidine.

Scheme 3. Synthesis of compounds 4a-c

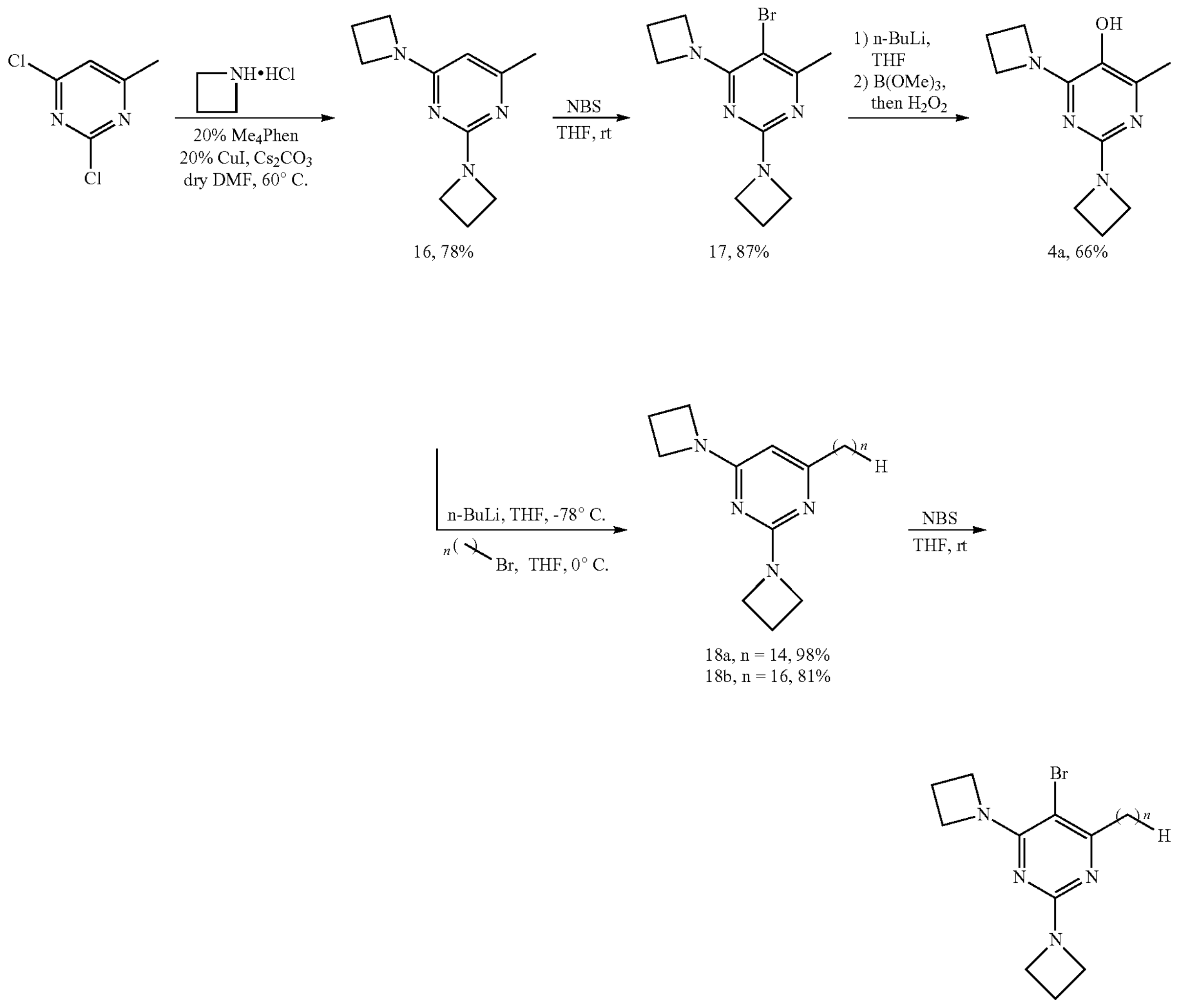

16, 78%

17, 87%

4a, 66%

18a, n = 14, 98%
18b, n = 16, 81%

19a, n = 14, 98%
19b, n = 16, 91%

-continued

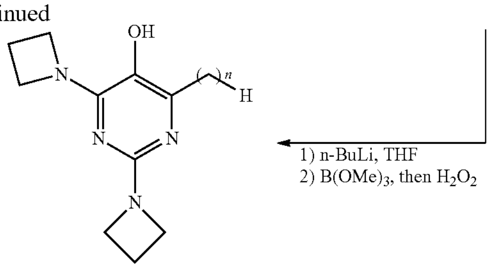

4b, n = 14, 53%
4c, n = 16, 66%

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

EXAMPLES

Chemistry

Anhydrous grade solvents were purchased from Sigma-Aldrich Inc. (St. Louis, MO) and from Fisher Scientific. Most of the chemical reagents were purchased from Sigma-Aldrich and used without further purification. $ImPrPh_2HCl$, morpholine and iodine were purchased from TCI America. Azetidine hydrochloride was purchased from Combi-Blocks. All glassware and needles were pre-dried in an oven at 120° C. prior to use. Tetrahydrofuran was distilled from sodium/benzophenone. All reactions were performed under a stream of argon. Flash column chromatography was carried out using silica gel (Silicycle R10030B, 60 Å particle size, 230-400 mesh), applying a low pressure stream of nitrogen. Analytical thin layer chromatographic separations were carried out on silica gel (60 Å particle size, 250 lm thickness, F-254, Silicycle) coated glass plates. Spots were visualized with UV light, or developed by using iodine vapor, or by immersing the plates in 2.0% anisaldehyde in ethanol/sulfuric acid/acetic acid, followed by heating with a heat gun. The NMR spectra were recorded using a 400 MHz Varian Inova instrument. Chemical shifts were reported in parts per million (ppm, d) relative to the residual 1H resonance of the solvent $CDCl_3$ or $CD_3OD$ at 7.26 ppm or 3.31 ppm, respectively. $^{13}C$ NMR chemical shifts were reported relative to the central line of $CDCl_3$ or $CD_3OD$ at 77.16 ppm or 49.00 ppm, respectively. Splitting patterns were designated as follows: s, singlet; br s, broad singlet; d, doublet; t, triplet; m, multiplet; quint, quintet. High resolution mass spectra were obtained at the Arizona State University CLAS High Resolution Mass Spectrometry Laboratory.

Example 1. Synthesis of 2-(Azetidin-1-yl)-4-cyclobutanoxy-6-methylpyrimidin-5-ol (1a)

Step 1. Synthesis of 2-(Azetidin-1-yl)-4-cyclobutoxy-6-methylpyrimidine (5a)

To a stirred solution of 1.40 g (19.4 mmol) of cyclobutanol in 100 mL of freshly distilled THF under argon was slowly added 1.55 g (38.8 mmol) of NaH (60% in paraffin) and the reaction mixture was stirred at room temperature for 30 min. The cooled (0° C.) reaction mixture was treated dropwise with 3.00 g (18.5 mmol) of the 2,4-dichloro-6-methylpyrimidine in solution in 10 mL of distilled THF. The reaction mixture was allowed to warm to room temperature and was maintained under argon for 4 h. After the reaction was complete, as judged by silica gel TLC, the reaction mixture was poured slowly into 100 mL of deionized water. The aqueous layer was extracted with three 100-mL portions of ethyl acetate. The combined organic phase was dried over $MgSO_4$ and concentrated to dryness under diminished pressure. The crude product was recovered as a yellowish oil and was used directly for the next step.

To 1.00 g (5 mmol) of the crude mixture was added 3.25 g (10.0 mmol) of $Cs_2CO_3$ and 936 mg (10.0 mmol) of azetidine hydrochloride in 30 mL of dry, degassed DMF. The suspension was stirred under argon at room temperature for 10 min and 118 mg (0.50 mmol) of 3,4,7,8-tetramethyl-1,10-phenanthroline and 95.0 mg (0.50 mmol) of copper (I) iodide were added successively to the reaction mixture. The reaction mixture was then warmed to 50° C. and maintained under argon for 12 h. After the reaction was completed as judged by silica gel TLC, the reaction mixture was diluted in 30 mL of ethyl acetate and filtered through Celite. The filtrate was concentrated to dryness. The crude residue was purified by flash chromatography on a silica gel column (15×4 cm). Elution with 9:1 hexane/EtOAc afforded 5a as a colorless solid: yield 390 mg (35%); mp 60-61° C.; silica gel TLC $R_f$ 0.22 (4:1 hexane/EtOAc); $^1H$ NMR ($CDCl_3$) δ 1.58-1.70 (m, 1H), 1.76-1.84 (m, 1H), 2.05-2.17 (m, 2H), 2.24 (s, 3H), 2.29 (qt, 2H, J=7.4 Hz), 2.38 (m, 2H), 4.08 (t, 4H, J=7.5 Hz), 5.04 (qt, 1H, J=7.4 Hz) and 5.77 (s, 1H); $^{13}C$ NMR ($CDCl_3$) δ 13.6, 16.3, 24.2, 30.8, 50.2, 70.1, 95.0, 163.2, 168.2 and 169.6; mass spectrum (APCI), m/z 220.1445 $(M+H)^+$ ($C_{12}H_{18}N_3O$ requires m/z 220.1450).

Step 2. Synthesis of 2-(Azetidin-1-yl)-5-bromo-4-cyclobutanoxy-6-methylpyrimidine (6)

To a stirred solution containing 112 mg (0.50 mmol) of 5a in 7 mL of freshly distilled $CH_2Cl_2$ at room temperature in the dark was added 178 mg (0.52 mmol) of recrystallized N-bromosuccinimide. The reaction mixture was stirred under argon for 1 hour at room temperature. The solvent was removed under diminished pressure and the resulting residue was purified by flash chromatography on a silica gel column (15×3 cm). Elution with 99:1 to 98:2 hexane/EtOAc afforded compound 6 as a colorless solid: yield 150 mg (98%); mp 84° C.; silica gel TLC $R_f$ 0.25 (9:1 hexane/EtOAc); $^1H$ NMR ($CDCl_3$) δ 1.62 (m, 1H), 1.80 (m, 1H), 2.16 (m, 2H), 2.27 (qt, 2H, J=7.4 Hz), 2.36-2.40 (m, 5H), 4.03 (t, 4H, J=7.5 Hz) and 5.10 (qt, 1H, J=7.4 Hz); $^{13}C$ NMR ($CDCl_3$) δ 13.6, 16.1, 24.4, 30.7, 50.2, 71.3, 92.8, 166.0, 164.5 and 160.8; mass spectrum (APCI), m/z 298.0552 $(M+H)^+$ ($C_{12}H_{17}{}^{79}BrN_3O$ requires m/z 298.0555) and m/z 300.0529 $(M+H)^+$ ($C_{12}H_{17}{}^{81}BrN_3O$ requires m/z 300.0535).

Step 3. Synthesis of 2-(Azetidin-1-yl)-4-cyclobutanoxy-6-methylpyrimidin-5-ol (1a)

A stirred solution containing 141 mg (0.49 mmol) of 6 in 5 mL of freshly distilled THF was cooled to −78° C. and maintained under argon for 10 min. To the resulting suspension was added 321 μL (0.51 mmol) of a 1.6 M solution of n-BuLi in hexane and the resulting reaction mixture was stirred at −78° C. for 1 h, resulting in a clear, yellowish solution. Then 110 μL (0.98 mmol) of trimethyl borate was added slowly and the reaction mixture was maintained at 0° C. for 1 additional hour. A solution of 300 μL of $H_2O_2$ (30% v/v) was then added and the reaction mixture was allowed to warm to room temperature and stirred for 30 min. The reaction mixture was diluted by the addition of 50 mL of satd aq $NH_4Cl$ and extracted with two 30-mL portions of $CH_2Cl_2$. The combined organic phase was dried over $MgSO_4$ and concentrated under diminished pressure. The residue was purified by flash chromatography on a silica gel column (15×1 cm). Elution with 9:1 to 2:1 hexane/EtOAc afforded compound 1a as a colorless solid: yield 98 mg (90%); mp 198° C.; silica gel TLC $R_f$ 0.4 (2:1 hexane/EtOAc); $^1H$ NMR ($CDCl_3$) δ 1.57 (m, 1H), 1.70 (m, 1H), 2.00 (m, 2H), 2.07 (s, 3H), 2.13 (qt, 2H, J=7.4 Hz), 2.29 (q, 2H, J=7.4 Hz), 3.80 (t, 4H, J=7.4 Hz), 4.98 (qt, 1H, J=7.4 Hz) and 7.82 (s, 1H); $^{13}C$ NMR (DMSO-d6) δ 13.1, 15.6, 18.2, 30.4, 50.3, 69.7, 128.0, 153.0, 156.6 and 158.5; mass spectrum (APCI), m/z 236.1398 $(M+H)^+$ ($C_{12}H_{18}N_3O_2$ requires m/z 236.1399).

Example 2. Synthesis of 2-(Azetidin-1-yl)-4-cyclobutanoxy-6-tetradecylpyrimidin-5-ol (1b)

Step 1. Synthesis of 2-(Azetidin-1-yl)-4-cyclobutanoxy-6-tetradecylpyrimidine (7a)

A stirred solution containing 112 mg (0.50 mmol) of 5a in 3 mL of freshly distilled THE was cooled under argon at −78° C. and maintained under argon for 15 min. A solution containing 273 μL (0.54 mmol) of 1.6 M n-BuLi in hexane was added dropwise and the resulting reaction mixture was stirred at −78° C. for 1 h. A solution of 131 mg (0.50 mmol) of 1-bromotridecane in 200 μL of distilled THE was then added dropwise and the reaction mixture was allowed to warm to 0° C. and was stirred for 1 h. The reaction was quenched by the addition of 20 mL of satd aq $NH_4Cl$, and then extracted with two 15-mL portions of $CH_2Cl_2$. The combined organic phase was dried over $MgSO_4$ and concentrated under diminished pressure. The residue was purified by flash chromatography on a silica gel column (15×2 cm). Elution with 98:2 to 95:5 hexane/EtOAc to afford compound 7a as a colorless solid: yield 154 mg (76%); mp 43-44° C.; silica gel TLC $R_f$ 0.5 (9:1 hexane/EtOAc); $^1H$ NMR ($CDCl_3$) δ 0.87 (t, 3H, J=6.6 Hz), 1.12-1.35 (m, 22H), 1.55-1.70 (m, 3H), 1.80 (m, 1H), 2.07-2.18 (m, 2H), 2.25-2.32 (m, 2H), 2.34-2.44 (m, 2H), 2.47 (t, 2H, J=7.6 Hz), 4.09 (t, 4H, J=7.5 Hz), 5.06 (qt, 1H, J=7.4 Hz) and 5.78 (s, 1H); $^{13}C$ NMR ($CDCl_3$) δ 13.7, 14.2 16.3, 22.8, 28.8, 29.5, 29.5, 29.6, 29.7, 29.8, 29.82, 29.83, 30.85, 32.1, 38.0, 50.2, 70.1, 94.3, 163.4, 169.6 and 172.5; mass spectrum (APCI), m/z 402.3490 $(M+H)^+$ ($C_{25}H_{44}N_3O$ requires m/z 402.3484).

Step 2. Synthesis of 2-(Azetidin-1-yl)-5-bromo-4-cyclobutanoxy-6-tetradecylpyrimidine (8a)

To a stirred solution containing 135 mg (0.36 mmol) of 7a in 5 mL of freshly distilled $CH_2Cl_2$ at room temperature in the dark was added 63 mg (0.38 mmol) of recrystallized N-bromosuccinimide. The reaction mixture was stirred under argon for 1 h at room temperature. The solvent was concentrated under diminished pressure and the resulting residue was purified by flash chromatography on a silica gel column (15×2 cm). Elution with 98:2 hexane/EtOAc afforded compound 8a as a colorless solid: yield 150 mg (93%); mp 71-72° C.; silica gel TLC $R_f$ 0.5 (9:1 hexane/AcOEt); $^1H$ NMR ($CDCl_3$) δ 0.88 (t, 3H, J=6.6 Hz), 1.20-1.35 (m, 22H), 1.58-1.70 (m, 3H), 1.78-1.86 (m, 1H), 2.13-2.22 (m, 2H), 2.25-2.33 (m, 2H), 2.39-2.46 (m, 2H), 2.67-2.71 (m, 2H), 4.06 (t, 4H, J=7.5 Hz) and 5.13 (qt, 1H, J=7.4 Hz); $^{13}C$ NMR ($CDCl_3$) δ 13.7, 14.2, 16.2, 22.8, 29.5, 29.6, 29.7, 29.8, 29.82, 29.83, 30.8, 32.1, 37.0, 50.3, 71.3, 92.7, 161.1, 164.7 and 169.5; mass spectrum (APCI), m/z 480.2561 $(M+H)^+$ ($C_{25}H_{43}{}^{79}BrN_3O$ requires m/z 480.2589) and m/z 482.2560 $(M+H)^+$ ($C_{25}H_{43}{}^{81}BrN_3O$ requires m/z 482.2569).

Step 3. Synthesis of 2-(Azetidin-1-yl)-4-cyclobutanoxy-6-tetradecylpyrimidin-5-ol (1b)

A stirred solution containing 150 mg (0.31 mmol) of 8b in 2 mL of freshly distilled THE was cooled to −78° C. and maintained under argon for 10 min. To the resulting suspension was added 234 μL (0.33 mmol) of 1.6 M n-BuLi in hexane and the resulting reaction mixture was stirred at −78° C. for 1 h, resulting in a clear, yellowish solution. Then 60 μL (0.62 mmol) of trimethyl borate was added slowly and the reaction was maintained at 0° C. for 1 additional hour. A solution of 400 μL of $H_2O_2$ (30% v/v) was then added and the reaction mixture was allowed to warm to room temperature and stirred for 30 min. The reaction mixture was diluted by addition of 50 mL of satd aq $NH_4Cl$ and extracted with two 20-mL portions of $CH_2Cl_2$. The combined organic phase was dried over $MgSO_4$ and concentrated under diminished pressure. The residue was purified by flash chromatography on a silica gel column (15×1 cm). Elution with 98:2 to 9:1 hexane/EtOAc afforded compound 1b as a colorless solid: yield 112 mg (86%); mp 100° C.; silica gel TLC $R_f$ 0.2 (9:1 hexane/EtOAc); $^1H$ NMR ($CDCl_3$) δ 0.88 (t, 3H, J=6.6 Hz), 1.20-1.35 (m, 22H), 1.55-1.70 (m, 3H), 1.83 (m, 1H), 2.06-2.16 (m, 2H), 2.26 (qt, 2H, J=7.2 Hz), 2.37-2.45 (m, 2H), 2.61 (m, 2H), 4.01 (t, 4H, J=7.2 Hz), 4.76 (br s, 1H) and 5.17 (qt, 1H, J=7.4 Hz); $^{13}C$ NMR ($CDCl_3$) δ 13.6, 14.3, 16.3, 22.8, 28.2, 29.5, 29.71, 29.73, 29.8, 29.81, 29.86, 29.9, 30.9, 31.5, 32.1, 50.9, 70.8, 128.1, 155.2, 157.6, 157.8; mass spectrum (APCI), m/z 418.3417 $(M+H)^+$ ($C_{25}H_{44}N_3O_2$ requires m/z 418.3434).

Example 3. Synthesis of 2-(Azetidin-1-yl)-4-cyclobutoxy-6-hexadecylpyrimidin-5-ol (1c)

Step 1. Synthesis of 2-(Azetidin-1-yl)-4-cyclobutoxy-6-hexadecylpyrimidine (7b)

A stirred solution containing 242 mg (1.07 mmol) of 5a in 10 mL of freshly distilled THE was cooled under argon at −78° C. and maintained under argon for 15 min. A solution of 739 μL (1.18 mmol) of 1.6 M n-BuLi in hexane was added dropwise and the resulting reaction mixture was stirred at −78° C. for 1 h. A solution of 319 mg (1.07 mmol) of 1-bromopentadecane in 500 μL of distilled THE was then added dropwise and the reaction mixture was allowed to warm to 0° C. and was stirred for 1 h. The reaction was quenched by the addition of 30 mL of satd aq $NH_4Cl$, and extracted with two 25-mL portions of $CH_2Cl_2$. The combined organic phase was dried over $MgSO_4$ and concentrated under diminished pressure. The residue was purified by flash chromatography on a silica gel column (15×2 cm). Elution with 98:2 to 95:5 hexane/EtOAc afforded compound 7b as a colorless solid: yield 389 mg (84%); mp 39-40° C.; silica gel TLC $R_f$ 0.5 (9:1 hexane/EtOAc); $^1H$ NMR ($CDCl_3$) δ 0.87 (t, 3H, J=6.6 Hz), 1.20-1.35 (m, 26H), 1.58-1.70 (m, 3H), 1.76-1.85 (m, 1H), 2.07-2.18 (m, 2H), 2.25-2.32 (m, 2H), 2.35-2.45 (m, 2H), 2.70 (t, 2H, J=7.6 Hz), 4.08 (t, 4H, J=7.5 Hz), 5.06 (qt, 1H, J=7.4 Hz) and 5.78 (s, 1H); $^{13}C$ NMR ($CDCl_3$) δ 13.7, 14.2 16.3, 22.8, 28.8, 29.5, 29.5, 29.6, 29.7, 29.8, 29.8, 29.8, 30.8, 32.1, 38.0, 50.2, 70.1, 94.3, 163.4, 169.6 and 172.5; mass spectrum (FAB), m/z 430.3786 $(M+H)^+$ ($C_{25}H_{48}N_3O$ requires m/z 430.3797).

Step 2. Synthesis of 2-(Azetidin-1-yl)-5-bromo-4-cyclobutoxy-6-hexadecylpyrimidine (8b)

To a stirred solution containing 340 mg (0.79 mmol) of 7b in 8 mL of freshly distilled $CH_2Cl_2$ at room temperature in the dark was added 147 mg (0.83 mmol) of recrystallized N-bromosuccinimide. The reaction mixture was stirred under argon for 1 h at room temperature. The solvent was removed under diminished pressure and the residue was purified by flash chromatography on a silica gel column (15×2 cm). Elution with 99:1 to 98:2 hexane/EtOAc afforded compound 8b as a colorless solid:yield 389 mg (96%); mp 84° C. silica gel TLC $R_f$ 0.25 (9:1 hexane/EtOAc); mp 71-73° C. silica gel TLC $R_f$ 0.5 (95:5 hexane/EtOAc); $^1H$ NMR ($CDCl_3$) δ 0.88 (t, 3H, J=6.6 Hz), 1.2-1.35 (m, 26H), 1.58-1.70 (m, 3H), 1.78-1.86 (m, 1H), 2.13-2.22 (m, 2H), 2.25-2.33 (m, 2H), 2.39-2.46 (m, 2H), 2.67-2.71 (m, 2H), 4.06 (t, 4H, J=7.5 Hz) and 5.13 (qt, 1H, J=7.4 Hz); $^{13}C$ NMR ($CDCl_3$) δ 13.7, 14.2, 16.2, 22.8, 28.0, 29.5, 29.6, 29.7, 29.8, 29.8, 29.81, 29.9, 30.8, 32.1, 37.0, 50.3, 71.3, 92.7, 161.1, 164.7 and 169.5; mass spectrum (FAB), m/z 508.2897 $(M+H)^+$ ($C_{25}H_{47}BrN_3O$ requires m/z 508.2902).

Step 3. Synthesis of 2-(Azetidin-1-yl)-4-cyclobutoxy-6-hexadecylpyrimidin-5-ol (1c)

A stirred solution containing 340 mg (0.67 mmol) of 5a in 7 mL of freshly distilled THE was cooled to −78° C. and maintained under argon for 10 min. To the resulting suspension was added 458 μL (0.73 mmol) of 1.6 M n-BuLi in hexane and the reaction mixture was stirred at −78° C. for 1 h resulting in a clear, yellowish solution. Then 120 μL (1.34 mmol) of trimethyl borate was added slowly and the reaction was maintained at 0° C. for 1 additional hour. A solution of 300 μL of $H_2O_2$ (30% v/v) was then added and the reaction mixture was allowed to warm to room temperature and stirred for 30 min. The reaction mixture was diluted by the addition of 50 mL of satd aq $NH_4Cl$ and extracted with two 30-mL portions of $CH_2Cl_2$. The combined organic phase was dried over $MgSO_4$ and concentrated under diminished pressure. The residue was purified by flash chromatography on a silica gel column (15×1 cm). Elution with 98:2 to 9:1 hexane/EtOAc to afford compound 1c as a colorless solid: yield 248 mg (84%); mp 95-97° C.; silica gel TLC $R_f$ 0.42 (4:1 hexane/EtOAc); $^1H$ NMR ($CDCl_3$) δ 0.88 (t, 3H, J=6.6 Hz), 1.2-1.35 (m, 26H), 1.55-1.70 (m, 3H), 1.83 (m, 1H), 2.06-2.16 (m, 2H), 2.26 (quint, 2H, J=7.2 Hz), 2.37-2.45 (m, 2H), 2.61 (m, 2H), 4.01 (t, 4H, J=7.2 Hz), 4.76 (br s, 1H) and 5.17 (qt, 1H, J=7.4 Hz); $^{13}C$ NMR ($CDCl_3$) δ 13.6, 14.3, 16.3, 22.8, 28.2, 29.5, 29.71, 29.73, 29.8, 29.81, 29.86, 29.9, 30.9, 31.5, 32.1, 50.9, 70.8, 128.1, 155.2, 157.6 and 157.8; mass spectrum (FAB), m/z 446.3742 $(M+H)^+$ ($C_{25}H_{48}N_3O_2$ requires m/z 446.3747).

Example 4. Synthesis of 4-(Azetidin-1-yl)-2-cyclobutanoxy-6-methylpyrimidin-5-ol (2a)

Step 1. Synthesis of 4-(Azetidin-1-yl)-2-cyclobutanoxy-6-methylpyrimidine (5b)

This compound was isolated as a side product from the reaction employed for the preparation of compound 5a after purification by flash chromatography on a silica gel column (15×4 cm). Elution with 2:1 hexane/EtOAc afforded 5b as a yellowish oil, yield 385 mg (34%); silica gel TLC $R_f$ 0.25 (2:1 hexane/EtOAc); $^1H$ NMR ($CDCl_3$) δ 1.54-1.66 (m, 1H), 1.73-1.82 (m, 1H), 2.12-2.22 (m, 2H), 2.24 (s, 3H), 2.34-2.42 (m, 4H), 4.05 (t, 4H, J=7.4 Hz), 5.12 (qt, 1H, J=7.4 Hz) and 5.64 (s, 1H); $^{13}C$ NMR ($CDCl_3$) δ 13.6, 16.7, 23.9, 30.8, 49.9, 70.4, 94.3, 164.2, 165.0 and 166.2; mass spectrum (APCI), m/z 220.1453 $(M+H)^+$ ($C_{12}H_{18}N_3O$ requires m/z 220.1450).

Step 2. Synthesis of 4-(Azetidin-1-yl)-5-bromo-2-cyclobutanoxy-6-methylpyrimidine (11)

To a stirred solution containing 280 mg (1.28 mmol) of 5b in 12 mL of freshly distilled $CH_2Cl_2$ at room temperature in the dark was added 236 mg (1.3 mmol) of recrystallized N-bromosuccinimide. The reaction mixture was stirred under argon for 1 h. The solvent was removed under diminished pressure and the resulting residue was purified by flash chromatography on a silica gel column (15×2 cm). Elution with 95:5 to 9:1 hexane/EtOAc to afford compound 11 as a colorless solid: yield 360 mg (95%); mp 55° C. silica gel TLC $R_f$ 0.2 (9:1 hexane/EtOAc); $^1H$ NMR ($CDCl_3$) δ 1.48-1.60 (m, 1H), 1.68-1.78 (m, 1H), 2.05-2.14 (m, 2H), 2.22 (qt, 2H, J=7.8 Hz), 2.27-2.37 (m, 2H), 2.31 (s, 3H), 4.30 (t, 4H, J=7.4 Hz) and 4.97 (qt, 1H, J=7.4 Hz); $^{13}C$ NMR ($CDCl_3$) δ 13.4, 16.1, 24.5, 30.6, 52.9, 70.7, 93.6, 160.6, 162.1 and 165.9; mass spectrum (APCI), m/z 298.0547 $(M+H)^+$ ($C_{12}H_{17}{}^{79}BrN_3O$ requires m/z 298.0555), m/z 300.0525 $(M+H)^+$ ($C_{12}H_{17}{}^{81}BrN_3O$ requires m/z 300.0535).

Step 3. Synthesis of 4-(Azetidin-1-yl)-2-cyclobutanoxy-6-methylpyrimidin-5-ol (2a)

A stirred solution containing 150 mg (0.51 mmol) of 11 in 7 mL of freshly distilled THE was cooled to −78° C. and maintained under argon for 10 min. To the resulting suspension was added 330 μL of 1.6 M BuLi in hexane (0.53 mmol) and the resulting reaction mixture was stirred at −78° C. for 1 h, resulting in a clear yellowish solution. A solution containing 117 μL (1.06 mmol) of trimethyl borate was added slowly and the reaction was maintained at 0° C. for 1 additional hour. A solution of 400 μL of $H_2O_2$ (30% v/v) was then added and the reaction mixture was allowed to warm to room temperature and was then stirred for 30 min. The reaction mixture was diluted by addition of 50 mL of satd aq $NH_4Cl$ and extracted with two 30-mL portions of $CH_2Cl_2$. The combined organic phase was combined, dried over $MgSO_4$ and concentrated under diminished pressure. The residue was purified by flash chromatography on a silica gel column (15×1 cm). Elution with 9:1 to 1:1 hexane/EtOAc to afford compound 2a as a colorless solid: yield 88 mg (73%); mp 59° C.; silica gel TLC $R_f$ 0.15 (1:1 hexane/EtOAc); $^1H$ NMR (DMSO-d6) δ 1.56 (m, 1H, J=8.7 Hz), 1.70 (q, 1H, J=9.8 Hz), 1.94 (qt, 2H, J=10.6 Hz), 2.09 (s, 3H), 2.18-2.35 (m, 4H), 4.11 (t, 4H, J=7.4 Hz), 4.90 (qt, 1H, J=7.3 Hz) and 7.74 (s, 1H); $^{13}C$ NMR ($CDCl_3$) δ 13.0, 26.6, 18.2, 30.3, 51.7, 69.1, 130.4, 151.5, 156.8 and 157.3; mass spectrum (APCI), m/z 236.1403 $(M+H)^+$ ($C_{12}H_{18}N_3O_2$ requires m/z 236.1399).

Example 5. Synthesis of 4-(Azetidin-1-yl)-2-cyclobutanoxy-6-tetradecylpyrimidin-5-ol (2b)

Step 1. Synthesis of 4-(Azetidin-1-yl)-2-cyclobutanoxy-6-tetradecylpyrimidine (9a)

A stirred solution containing 342 mg (1.56 mmol) of 5b in 10 mL of freshly distilled THF was cooled under argon at −78° C. and maintained under argon for 15 min. A solution containing 1.00 mL (1.60 mmol) of 1.6 M n-BuLi in hexane was added dropwise and the resulting reaction mixture was stirred at −78° C. for 1 h. A solution of 420 mg (1.60 mmol) of 1-bromotridecane in solution in 1 mL of distilled THE was then added dropwise and the reaction mixture was allowed to warm to 0° C. and stirred for 1 h. The reaction was quenched by adding 40 mL of satd aq $NH_4Cl$ and then extracted with two 35-mL portions of $CH_2Cl_2$. The combined organic phase was dried over $MgSO_4$ and concentrated under diminished pressure. The residue was purified by flash chromatography on a silica gel column (15×2 cm). Elution with 98:2 to 95:5 hexane/EtOAc afforded compound 9a as a colorless solid: yield 583 mg (95%); mp 182° C.; silica gel TLC $R_f$ 0.15 (9:1 hexane/EtOAc); $^1H$ NMR ($CDCl_3$) δ 0.86 (t, 3H, J=6.6 Hz), 1.2-1.35 (m, 22H), 1.53-1.68 (m, 3H), 1.73-1.81 (m, 1H), 2.12-2.22 (m, 2H), 2.33-2.46 (m, 4H), 2.45 (m, 2H), 4.04 (t, 4H, J=7.5 Hz), 5.11 (qt, 1H, J=7.4 Hz) and 5.61 (s, 1H); $^{13}C$ NMR ($CDCl_3$) δ 13.6, 14.2, 16.7, 22.8, 28.6, 29.5, 29.6, 29.7, 29.77, 29.79, 29.8, 29.82, 30.8, 32.0, 37.9, 49.9, 70.3, 93.8, 164.5, 165.1 and 170.7; mass spectrum (APCI), m/z 402.3496 $(M+H)^+$ ($C_{25}H_{44}N_3O$ requires m/z 402.3484).

Step 2. Synthesis of 4-(Azetidin-1-yl)-5-bromo-2-cyclobutanoxy-6-tetradecylpyrimidine (10a)

To a stirred solution containing 536 mg (1.12 mmol) of 9a in 20 mL of freshly distilled $CH_2Cl_2$ at room temperature in the dark was added 204 mg (1.15 mmol) of recrystallized N-bromosuccinimide. The reaction mixture was stirred under argon for 1 h at room temperature. The solvent was concentrated under diminished pressure and the resulting residue was purified by flash chromatography on a silica gel column (15×2 cm). Elution with 98:2 hexane/EtOAc to afford compound 10a as a colorless solid: yield 582 mg (91%); mp 52° C.; silica gel TLC $R_f$ 0.5 (9:1 hexane/EtOAc); $^1H$ NMR ($CDCl_3$) δ 0.87 (t, 3H, J=6.6 Hz), 1.18-1.38 (m, 22H), 1.55-1.68 (m, 3H), 1.73-1.82 (m, 1H), 2.12-2.22 (m, 2H), 2.22-2.30 (m, 2H), 2.33-2.42 (m, 2H), 2.66 (m, 2H), 4.37 (t, 4H, J=7.5 Hz) and 5.03 (qt, 1H, J=7.4 Hz); $^{13}C$ NMR ($CDCl_3$) δ 13.6, 14.3, 16.3, 22.8, 27.8, 29.5, 29.58 29.61, 29.7, 29.80, 29.82, 29.84, 30.7, 32.1, 37.9, 53.1, 71.0, 93.8, 161.1, 162.4 and 169.4; mass spectrum (APCI), m/z 480.2580 $(M+H)^+$ ($C_{25}H_{43}{}^{79}BrN_{30}$ requires m/z 480.2589), m/z 482.2570 $(M+H)^+$ ($C_{25}H_{43}{}^{81}BrN_3O$ requires m/z 482.2569).

Step 3. Synthesis of 4-(Azetidin-1-yl)-2-cyclobutanoxy-6-tetradecylpyrimidin-5-ol (2b)

A stirred solution containing 200 mg (0.41 mmol) of 10a in 4 mL of freshly distilled THE was cooled to −78° C. and maintained under argon for 10 min. To the resulting suspension was added 274 μL of 1.6 M n-BuLi in hexane (0.44 mmol) and the resulting reaction mixture was stirred at −78° C. for 1 h, resulting in a clear yellowish solution. A sample of 50 μL (0.82 mmol) of trimethyl borate was added slowly and the reaction was maintained at 0° C. for 1 additional hour. A solution of 500 μL of $H_2O_2$ (30% v/v) was then added and the reaction mixture was allowed to warm to room temperature and stirred for 30 min. The reaction mixture was diluted by the addition of 50 mL of satd aq $NH_4Cl$ and was then extracted with two 30-mL portions of $CH_2Cl_2$. The combined organic phase was dried over $MgSO_4$ and concentrated under diminished pressure. The residue was purified by flash chromatography on a silica gel column (15×1 cm). Elution with 98:2 to 9:1 hexane/EtOAc afforded compound 2b as a colorless solid: yield 116 mg (68%); mp 84° C.; silica gel TLC $R_f$ 0.45 (2:1 hexane/EtOAc); $^1H$ NMR ($CDCl_3$) δ 0.88 (t, 3H, J=6.6 Hz), 1.20-1.36 (m, 22H), 1.54-1.68 (m, 3H), 1.71-1.81 (m, 1H), 2.09-2.20 (m, 2H), 2.26-2.40 (m, 4H), 2.49 (m, 2H), 4.26 (t, 4H, J=7.5 Hz) and 5.02 (qt, 1H, J=7.5 Hz); $^{13}C$ NMR ($CDCl_3$) δ 13.6, 14.3, 17.4, 22.8, 27.9, 29.52, 29.70, 29.74, 29.83, 31.1, 32.1, 52.3, 70.5, 130.1, 154.8, 156.8 and 158.4; HRMS (APCI), m/z 418.3443 $(M+H)^+$ ($C_{25}H_{44}N_3O_2$ requires m/z 418.3434).

Example 6. Synthesis of 4-(Azetidin-1-yl)-2-cyclobutanoxy-6-hexadecylpyrimidin-5-ol (2c)

Step 1. Synthesis of 4-(Azetidin-1-yl)-2-cyclobutanoxy-6-hexadecylpyrimidine (9b)

A stirred solution containing 215 mg (0.96 mmol) of 5b in 10 mL of freshly distilled THF was cooled under argon at −78° C. and maintained under argon for 15 min. A solution containing 631 μL (1.01 mmol) of 1.6 M n-BuLi in hexane was added dropwise and the resulting reaction mixture was stirred at −78° C. for 1 h. A solution of 278 mg (0.96 mmol) of 1-bromopentadecane in 500 μL of distilled THE was then added dropwise and the reaction was then allowed to warm to 0° C. and stirred for 1 h. The reaction was quenched by the addition of 40 mL of satd aq $NH_4Cl$ and extracted with two 35-mL portions of $CH_2Cl_2$. The combined organic phase was dried over $MgSO_4$ and concentrated under diminished pressure. The residue was purified by flash chromatography on a silica gel column (15×2 cm). Elution with 9:1 to 1:1 hexane/EtOAc afforded compound 9b as a colorless solid: yield 362 mg (88%); mp 179° C.; silica gel TLC $R_f$ 0.15 (9:1 hexane/EtOAc); $^1H$ NMR ($CDCl_3$) δ 0.85 (t, 3H, J=6.6 Hz), 1.18-1.34 (m, 26H), 1.53-1.65 (m, 3H), 1.75 (qt, 1H, J=9.9 Hz), 2.16 (qt, 2H, J=9.9 Hz), 2.30-2.39 (m, 4H), 2.43 (t, 2H, J=8.1 Hz), 4.02 (t, 4H, J=7.5 Hz), 5.09 (qt, 1H, J=7.4 Hz) and 5.60 (s, 1H); $^{13}C$ NMR ($CDCl_3$) δ 13.6, 14.2, 16.7, 22.8, 28.6, 29.4, 29.6, 29.7, 29.75, 29.8, 30.8, 32.0, 37.9, 49.8, 70.3, 93.7, 164.5, 165.1 and 170.7; HRMS (APCI), m/z 430.3795 $(M+H)^+$ ($C_{27}H_{48}N_3O$ requires m/z 430.3797).

Step 2. Synthesis of 4-(Azetidin-1-yl)-5-bromo-2-cyclobutanoxy-6-hexadecylpyrimidine (10b)

To a stirred solution containing 208 mg (0.48 mmol) of 9b dissolved in 5 mL of freshly distilled $CH_2Cl_2$ at room temperature in the dark was added 90.0 mg (0.50 mmol) of recrystallized N-bromosuccinimide. The reaction mixture was stirred under argon for 1 h at room temperature. The solvent was concentrated under diminished pressure and the resulting residue was purified by flash chromatography on a silica gel column (15×2 cm). Elution with 98:2 to 95:5 hexane/EtOAc afforded compound 10b as a colorless solid: yield 231 mg (91%); mp 56° C.; silica gel TLC $R_f$ 0.5 (9:1 hexane/EtOAc); $^1H$ NMR ($CDCl_3$) δ 0.87 (t, 3H, J=6.6 Hz), 1.12-1.35 (m, 26H), 1.55-1.68 (m, 3H), 1.77-1.81 (m, 1H), 2.06-2.28 (m, 4H), 2.28-2.38 (m, 2H), 2.66 (t, 2H, J=7.5 Hz), 4.37 (t, 4H, J=7.5 Hz) and 5.03 (qt, 1H, J=7.4 Hz); $^{13}C$ NMR ($CDCl_3$) δ 13.5, 14.2, 16.2, 22.8, 27.7, 29.4, 29.5, 29.55, 29.6, 29.7, 29.8, 30.7, 32.0, 53.0, 70.9, 93.7, 161.0, 162.3 and 169.3; mass spectrum (APCI), m/z 508.2904 $(M+H)^+$ ($C_{27}H_{47}{}^{79}BrN_{30}$ requires m/z 508.2902), m/z 510.3906 $(M+H)^+$ ($C_{27}H_{47}{}^{81}BrN_3O$ requires m/z 510.3916).

Step 3. Synthesis of 4-(Azetidin-1-yl)-2-cyclobutanoxy-6-hexadecylpyrimidin-5-ol (2c)

A stirred solution containing 200 mg (0.39 mmol) of 10b in 4 mL of freshly distilled THF was cooled to −78° C. and maintained under argon for 10 min. To the resulting suspension was added 259 μL of 1.6 M n-BuLi in hexane (0.41 mmol) and the resulting reaction mixture was stirred at −78° C. for 1 h, resulting in a clear yellowish solution. A sample of 86 μL (0.78 mmol) of trimethyl borate was added slowly and the reaction mixture was maintained at 0° C. for 1 additional hour. A solution of 500 μL of $H_2O_2$ (30% v/v) was then added and the reaction was allowed to warm to room temperature and stirred for 30 min. The reaction mixture was diluted by the addition of 50 mL of satd $NH_4Cl$ and extracted with two 30-mL portions of $CH_2Cl_2$. The combined organic phase was dried over $MgSO_4$ and concentrated under diminished pressure. The residue was purified by flash chromatography on a silica gel column (15×1 cm). Elution with 9:1 to 8:2 hexane/EtOAc afforded compound 2c as a colorless solid: yield 122 mg (70%); mp 85° C.; silica gel TLC $R_f$ 0.5 (2:1 hexane/EtOAc); $^1H$ NMR ($CDCl_3$) δ 0.86 (t, 3H, J=6.6 Hz), 1.18-1.35 (m, 26H), 1.49-1.60 (m, 3H), 1.68-1.75 (m, 1H), 2.09-2.20 (m, 2H), 2.20-2.35 (m, 4H), 2.43 (t, 2H, J=7.5 Hz), 4.24 (t, 4H, J=7.4 Hz), 4.95 (qt, 1H, J=7.4 Hz) and 6.36 (br s, 1H); $^{13}C$ NMR ($CDCl_3$) δ 13.5, 14.2, 17.3, 21.1, 22.8, 28.2, 29.79, 29.84, 29.86, 29.88, 30.7, 31.0, 32.0, 52.1, 70.3, 130.1, 156.0, 157.5 and 158.0; mass spectrum (APCI), m/z 446.3739 $(M+H)^+$ ($C_{27}H_{48}N_3O_2$ requires m/z 446.3747).

Example 7. Synthesis of 2,4-Dicyclobutanoxy-6-methylpyrimidin-5-ol (3a)

Step 1. Synthesis of 2,4-Dicyclobutanoxy-6-methylpyrimidine (12)

To a solution containing 1.66 g (23.0 mmol) of cyclobutanol in 60 mL of freshly distilled THF under argon was added slowly 1.84 g (46.0 mmol) of NaH (60% in paraffin) and the reaction mixture was stirred at room temperature for 20 min. The resulting suspension was cooled to 0° C. and 1.50 g (9.20 mmol) of 2,4-dichloro-6-methylpyrimidine was added in portions; the resulting yellow reaction mixture was stirred at room temperature overnight. After the reaction was completed, as judged by silica gel TLC analysis, the reaction mixture was poured slowly into 100 mL of water. The aqueous layer was extracted with two 50-mL portions of $CH_2Cl_2$. The combined organic phase washed with 50 mL of brine and dried over $MgSO_4$. The resulting solution was concentrated under diminished pressure. The crude mixture was purified by flash chromatography on a silica gel column (15×4 cm). Elution with 95:5 to 9:1 hexane/EtOAc afforded compound 12 as a colorless oil: yield 1.95 mg (91%); silica gel TLC $R_f$ 0.2 (95:5 hexane/EtOAc); $^1H$ NMR ($CDCl_3$) δ 1.55-1.67 (m, 2H), 1.72-1.83 (m, 2H), 2.04-2.20 (m, 4H), 2.27 (s, 3H), 2.32-2.44 (m, 4H), 5.09 (qt, 1H, J=7.5 Hz), 5.15 (qt, 1H, J=7.5 Hz) and 6.08 (s, 1H); $^{13}C$ NMR ($CDCl_3$) δ 13.49, 13.51, 23.9, 30.57, 30.63, 70.3, 70.9, 99.9, 164.1, 169.4 and 170.7; mass spectrum (APCI), m/z 235.1441 $(M+H)^+$ ($C_{13}H_{19}N_2O_2$ requires m/z 235.1447).

Step 2. Synthesis of 2,4-Dicyclobutoxy-5-bromo-6-methylpyrimidine (13)

To a stirred solution containing 280 mg (1.20 mmol) of 12 in 6 mL of freshly distilled $CH_2Cl_2$ at room temperature in the dark was added 425 mg (2.40 mmol) of recrystallized N-bromosuccinimide. The reaction mixture was stirred under argon for 72 h. The solvent was concentrated under diminished pressure and the resulting residue was purified by flash chromatography on a silica gel column (15×3 cm). Elution with 98:2 to 95:5 hexane/EtOAc afforded compound 13 as a colorless oil: yield 360 mg (96%); silica gel TLC $R_f$ 0.5 (9:1 hexane/EtOAc); $^1H$ NMR ($CDCl_3$) δ 1.59-1.70 (m, 2H), 1.76-1.88 (m, 2H), 2.11-2.25 (m, 4H), 2.34-2.5 (m, 7H), 5.05 (qt, 1H, J=7.4 Hz) and 5.20 (qt, 1H, J=7.4 Hz); $^{13}C$ NMR ($CDCl_3$) δ 13.49, 13.51, 24.4, 30.5, 30.6, 71.4, 71.8, 97.8, 162.1, 165.9 and 167.7; mass spectrum (APCI), m/z 313.0548 $(M+H)^+$ ($C_{13}H_{18}{}^{79}BrN_2O_2$ requires m/z 313.0552). m/z 315.0532 $(M+H)^+$ ($C_{13}H_{18}{}^{81}BrN_2O_2$ requires m/z 315.0531).

Step 3. Synthesis of 2,4-Dicyclobutanoxy-6-methylpyrimidin-5-ol (3a)

A stirred solution containing 200 mg (0.64 mmol) of 13 in 8 mL of freshly distilled THE was cooled to −78° C. and maintained under argon for 10 min. To the resulting suspension was added 400 μL (0.64 mmol) of 1.6 M n-BuLi in hexane and the resulting reaction mixture was stirred at −78° C. for 1 h leading to a clear yellowish solution. Then 141 μL (1.27 mmol) of trimethyl borate was added slowly and the reaction mixture was maintained at 0° C. for an additional hour. A solution of 500 μL of $H_2O_2$ (30% v/v) was then added and the reaction mixture was allowed to warm to room temperature and stirred for 30 min. The reaction mixture was diluted by the addition of 50 mL of satd aq $NH_4Cl$ and extracted with two 30-mL portions of $CH_2Cl_2$. The combined organic phase was dried over $MgSO_4$ and concentrated under diminished pressure. The residue was purified by flash chromatography on a silica gel column (15×1 cm). Elution with 95:5 to 9:1 hexane/EtOAc afforded compound 3a as a colorless solid: yield 105 mg (67%); mp 122° C.; silica gel TLC $R_f$ 0.15 (9:1 hexane/EtOAc); $^1H$ NMR ($CDCl_3$) δ 1.55-1.68 (m, 2H), 1.70-1.85 (m, 2H), 2.05-2.17 (m, 4H), 2.31 (s, 3H), 2.32-2.48 (m, 4H), 5.00 (qt, 1H, J=7.4 Hz), 5.21 (qt, 1H, J=7.4 Hz) and 5.38 (br s, 1H); $^{13}C$ NMR ($CDCl_3$) δ 13.49, 13.51, 24.4, 30.5, 30.6, 71.4, 71.8, 97.8, 162.1, 165.9 and 167.7; mass spectrum (APCI), m/z 251.1390 $(M+H)^+$ ($C_{13}H_{19}N_2O_3$ requires m/z 251.1396).

Example 8. Synthesis of 2,4-Dicyclobutanoxy-6-tetradecylpyrimidin-5-ol (3b)

Step 1. Synthesis of 2,4-Dicyclobutanoxy-6-tetradecylpyrimidine (14a)

A stirred solution containing 270 mg (1.15 mmol) of 12 in 5 mL of freshly distilled THE was cooled to −78° C. and maintained under argon. After 15 min, 790 μL (1.60 mmol) of 1.6 M n-BuLi in hexane was added dropwise and the resulting reaction mixture was stirred at −78° C. for 1 h. A solution containing 304 mg (1.15 mmol) of 1-bromotridecane in 1 mL of distilled THF was then added dropwise and the reaction mixture was allowed to warm to 0° C. and then stirred for 1 h. The reaction was quenched by the addition of 40 mL of satd aq $NH_4Cl$ and extracted with two 35-mL portions of $CH_2Cl_2$. The combined organic phase was dried over $MgSO_4$ and concentrated under diminished pressure. The residue was purified by flash chromatography on a silica gel column (15×2 cm). Elution with 98:2 to 95:5 hexane/EtOAc afforded compound 14a as a colorless oil: yield 440 mg (92%); silica gel TLC $R_f$ 0.4 (95:5 hexane/EtOAc); $^1H$ NMR ($CDCl_3$) δ 0.86 (t, 3H, J=6.5 Hz), 1.16-1.34 (m, 22H), 1.60-1.68 (m, 4H), 1.75-1.85 (m, 2H), 2.07-2.16 (m, 2H), 2.17-2.23 (m, 2H), 2.35-2.45 (m, 4H), 2.52 (m, 2H), 5.11 (qt, 1H, J=7.4 Hz), 5.18 (qt, 1H, J=7.5 Hz) and 6.10 (s, 1H); $^{13}C$ NMR ($CDCl_3$) δ 13.6, 14.2, 22.8, 27.5, 28.6, 29.4, 29.48, 29.55, 29.6, 29.8, 30.6, 30.7, 32.0, 34.8, 37.7, 70.3, 70.4, 70.9, 71.0, 99.4, 99.5, 164.3, 170.7 and 173.6; mass spectrum (APCI), m/z 417.3475 $(M+H)^+$ ($C_{26}H_{45}N_2O_2$ requires m/z 417.3481).

Step 2. Synthesis of 5-Bromo-2,4-dicyclobutoxy-6-tetradecylpyrimidine (15a)

To a stirred solution containing 300 mg (0.72 mmol) of 14a in 5 mL of freshly distilled $CH_2Cl_2$ at room temperature in the dark was added 256 mg (1.44 mmol) of recrystallized N-bromosuccinimide. The reaction mixture was stirred under argon for 72 h. The solvent was concentrated under diminished pressure and the resulting residue was purified by flash chromatography on a silica gel column (15×3 cm). Elution with 98:2 hexane/EtOAc afforded compound 15a as a colorless oil: yield 311 mg (87%); silica gel TLC $R_f$ 0.45 (95:5 hexane/EtOAc); $^1H$ NMR ($CDCl_3$) δ 0.88 (t, 3H, J=6.5 Hz), 1.20-1.40 (m, 22H), 1.61-1.700 (m, 4H), 1.79-1.90 (m, 2H), 2.15-2.27 (m, 4H), 2.37-2.51 (m, 4H), 2.76 (m, 2H), 5.08 (qt, 1H, J=7.5 Hz) and 5.23 (qt, 1H, J=7.6 Hz); $^{13}C$ NMR ($CDCl_3$) δ 13.6, 14.3, 22.8, 27.8, 29.5, 29.55, 29.7, 29.81, 29.82, 29.84, 30.6, 30.7, 32.1, 37.0, 71.5, 71.9, 97.7, 162.4, 166.1 and 171.1; mass spectrum (APCI), m/z 495.2591 $(M+H)^+$ ($C_{26}H_{44}{}^{79}BrN_2O_2$ requires m/z 495.2586) and m/z 497.2575 $(M+H)^+$ ($C_{26}H_{44}{}^{81}BrN_2O_2$ requires m/z 497.2566).

Step 3. Synthesis of 2,4-Dicyclobutanoxy-6-tetradecylpyrimidin-5-ol (3b)

A stirred solution containing 180 mg (0.36 mmol) of 15a in 5 mL of freshly distilled THE was cooled to −78° C. and maintained under argon for 10 min. To the resulting suspension was added slowly 225 μL (0.36 mmol) of 1.6 M n-BuLi in hexane and the resulting reaction mixture was stirred at −78° C. for 1 h leading to a clear yellowish solution. Then 80.0 μL (0.73 mmol) of trimethyl borate was added slowly and the reaction mixture was maintained at 0° C. for an additional hour. A solution of 200 μL of $H_2O_2$ (30% v/v) was then added and the reaction mixture was allowed to warm to room temperature and was stirred for 30 min. The reaction mixture was diluted by the addition of 20 mL of satd aq $NH_4Cl$ and extracted with two 15-mL portions of $CH_2Cl_2$. The combined organic phase was dried over $MgSO_4$ and concentrated under diminished pressure. The residue was purified by flash chromatography on a silica gel column (15×1 cm). Elution with 98:2 to 9:1 hexane/EtOAc afforded compound 3b as a colorless solid: yield 72 mg (46%); mp 60° C.; silica gel TLC $R_f$ 0.40 (9:1 hexane/EtOAc); $^1H$ NMR ($CDCl_3$) δ 0.87 (t, 3H, J=6.5 Hz), 1.15-1.38 (m, 22H), 1.58-1.72 (m, 4H), 1.76-1.88 (m, 2H), 2.08-2.22 (m, 4H), 2.35-2.51 (m, 4H), 2.64 (m, 2H), 4.80 (s, 1H), 5.02 (qt, 1H, J=7.5 Hz) and 5.25 (qt, 1H, J=7.5 Hz); $^{13}C$ NMR ($CDCl_3$) δ 13.5, 13.6, 14.2, 22.8, 27.7, 29.5, 29.60, 29.72, 29.81, 29.83, 29.84, 30.7, 30.9, 31.3, 32.1, 70.9, 71.2, 130.9, 155.8, 156.4 and 158.2; mass spectrum (APCI), m/z 433.3434 $(M+H)^+$ ($C_{26}H_{45}N_2O_3$ requires m/z 433.3430).

Example 9. Synthesis of 2,4-Dicyclobutanoxy-6-hexadecylpyrimidin-5-ol (3c)

Step 1. Synthesis of 2,4-Dicyclobutanoxy-6-hexadecylpyrimidine (14b)

A stirred solution containing 300 mg (1.28 mmol) of 12 in 5 mL of freshly distilled THE was cooled to −78° C. and maintained under argon. After 15 min, 800 μL (1.28 mmol) of 1.6 M n-BuLi in hexane was added dropwise and the reaction mixture was stirred at −78° C. for 1 h. A solution containing 372 mg (1.28 mmol) of 1-bromopentadecane in 1 mL of distilled THE was then added dropwise and the reaction mixture was allowed to warm to 0° C. and was stirred for 1 h. The reaction was quenched by the addition of 40 mL of satd aq $NH_4Cl$ and was extracted with two 35-mL portions of $CH_2Cl_2$. The combined organic phase was dried over $MgSO_4$ and concentrated under diminished pressure. The residue was purified by flash chromatography on a silica gel column (15×2 cm). Elution with 98:2 hexane/EtOAc afforded compound 14b as a colorless oil: yield 520 mg (91%); silica gel TLC $R_f$ 0.4 (95:5 hexane/EtOAc); $^1H$ NMR ($CDCl_3$) δ 0.85 (t, 3H, J=6.4 Hz), 1.16-1.32 (m, 26H), 1.58-1.65 (m, 4H), 1.75-1.85 (m, 2H), 2.06-2.15 (m, 2H), 2.15-2.24 (m, 2H), 2.35-2.45 (m, 4H), 2.52 (m, 2H), 5.10 (qt, 1H, J=7.5 Hz), 5.17 (qt, 1H, J=7.5 Hz) and 6.08 (s, 1H); $^{13}C$ NMR ($CDCl_3$) δ 13.6, 14.2, 22.8, 27.8, 28.5, 29.4, 29.5, 29.52, 29.6, 29.74, 29.76, 29.78, 29.79, 30.6, 30.7, 32.0, 37.7, 70.3, 70.9, 99.4, 164.3, 170.7 and 173.5; mass spectrum (APCI), m/z 445.3792 $(M+H)^+$ ($C_{28}H_{49}N_2O_2$ requires m/z 445.3794).

Step 2. Synthesis of 2,4-Dicyclobutoxy-5-bromo-6-hexadecylpyrimidine (15b)

To a stirred solution containing 200 mg (0.45 mmol) of 14b in 2 mL of freshly distilled $CH_2Cl_2$ at room temperature in the dark was added 160 mg (0.90 mmol) of recrystallized N-bromosuccinimide. The reaction mixture was stirred under argon for 72 h. The solvent was concentrated under diminished pressure and the resulting residue was purified by flash chromatography on a silica gel column (15×3 cm). Elution with 98:2 hexane/EtOAc afforded compound 15b as a colorless oil: yield 227 mg (96%); silica gel TLC $R_f$ 0.45 (95:5 hexane/EtOAc); $^1$H NMR ($CDCl_3$) δ 0.87 (t, 3H, J=6.6 Hz), 1.18-1.40 (m, 26H), 1.60-1.73 (m, 4H), 1.78-1.88 (m, 2H), 2.15-2.27 (m, 4H), 2.36-2.50 (m, 4H), 2.76 (m, 2H), 5.07 (qt, 1H, J=7.4 Hz) and 5.23 (qt, 1H, J=7.6 Hz); $^{13}$C NMR ($CDCl_3$) δ 13.5, 14.2, 22.8, 27.7, 29.5, 29.53, 29.67, 29.78, 29.79, 29.81, 29.83, 30.6, 30.7, 32.1, 37.0, 71.5, 71.8, 97.6, 162.4, 166.1 and 171.1; mass spectrum (APCI), m/z 523.2901 $(M+H)^+$ ($C_{28}H_{48}{}^{79}BrN_2O_2$ requires m/z 523.2899). m/z 525.2896 $(M+H)^+$ ($C_{28}H_{48}{}^{81}BrN_2O_2$ requires m/z 525.2879).

Step 3. Synthesis of 2,4-Dicyclobutanoxy-6-hexadecylpyrimidin-5-ol (3c)

A stirred solution containing 200 mg (0.38 mmol) of 15b in 5 mL of freshly distilled THF was cooled to −78° C. and kept under argon for 10 min. To the resulting suspension was added 240 μL (0.38 mmol) of 1.6 M n-BuLi in hexane and the resulting reaction mixture was stirred at −78° C. for 1 h resulting in a clear yellowish solution. Then 84.0 μL (0.76 mmol) of trimethyl borate was added slowly and the reaction mixture was maintained at 0° C. for 1 additional hour. A solution of 300 μL of $H_2O_2$ (30% v/v) was then added and the reaction mixture was allowed to warm to room temperature and stirred for 30 min. The reaction mixture was diluted by the addition of 30 mL of satd aq $NH_4Cl$ and extracted with two 20-mL portions of $CH_2Cl_2$. The combined organic phase was dried over $MgSO_4$ and concentrated under diminished pressure. The residue was purified by flash chromatography on a silica gel column (15×1 cm). Elution with 98:2 to 95:5 hexane/EtOAc afforded compound 3c as a colorless solid: yield 88 mg (52%); mp 67° C.; silica gel TLC $R_f$ 0.45 (9:1 hexane/EtOAc); $^1$H NMR ($CDCl_3$) δ 0.86 (t, 3H, J=6.7 Hz), 1.13-1.38 (m, 26H), 1.56-1.72 (m, 4H), 1.74-1.87 (m, 2H), 2.06-2.20 (m, 4H), 2.34-2.49 (m, 4H), 2.64 (m, 2H), 4.92 (br s, 1H), 5.02 (qt, 1H, J=7.5 Hz) and 5.24 (qt, 1H, J=7.6 Hz); $^{13}$C NMR ($CDCl_3$) δ 13.46, 13.54, 14.2, 22.8, 27.7, 29.5, 29.59, 29.60, 29.7, 29.78, 29.80, 29.83, 30.7, 30.8, 31.2, 32.0, 70.9, 71.2, 130.9, 155.9, 156.4 and 158.2; mass spectrum (APCI), m/z 461.3738 $(M+H)^+$ ($C_{28}H_{49}N_2O_3$ requires m/z 461.3743).

Example 10. Synthesis of 2,4-Di-(azetidin-1-yl)-6-methylpyrimidin-5-ol (4a)

Step 1. Synthesis of 2,4-Di-(azetidin-1-yl)-6-methylpyrimidine (16)

To a suspension containing 1.00 g (6.13 mmol) of 2,4-dichloro-6-methylpyrimidine and 10.7 g (30.6 mmol) of $Cs_2CO_3$ in 25 mL of dry, degassed DMF was added 2.29 g (24.5 mmol) of azetidine hydrochloride and a positive pressure of argon was applied. To the reaction mixture was added 144 mg (0.61 mmol) of 3,4,7,8-tetramethyl-1,10-phenanthroline and 116 mg (0.61 mmol) of copper (I) iodide, and the reaction mixture was stirred at 60° C. under argon for 48 h. After the reaction was complete as judged by silica gel TLC analysis, the reaction mixture was diluted in 30 mL of ethyl acetate and filtered through Celite. The filtrate was concentrated to dryness and the crude residue was purified by flash chromatography on a silica gel column (15×4 cm). Elution with 9:1, 1:1, and then 1:3 hexane/EtOAc afforded 16 as a yellowish solid: yield 986 mg (78%); mp 78-79° C.; silica gel TLC $R_f$ 0.2 (1:3 hexane/EtOAc); $^1$H NMR ($CDCl_3$) δ 2.20 (s, 3H), 2.26 (qt, 2H, J=7.6 Hz), 2.33 (qt, 2H, J=7.6 Hz), 3.99 (t, 4H, J=7.6 Hz), 4.07 (t, 4H, J=7.6 Hz) and 5.41 (s, 1H); $^{13}$C NMR ($CDCl_3$) δ 16.2, 16.7, 24.2, 49.7, 50.2, 90.8, 163.5, 164.4 and 165.1; mass spectrum (APCI), m/z 205.1451 $(M+H)^+$ ($C_{11}H_{17}N_4$ requires m/z 205.1453).

Step 2. Synthesis of 2,4-Di-(azetidin-1-yl)-5-bromo-6-methylpyrimidine (17)

To a stirred solution containing 205 mg (1.00 mmol) of 16 in 7 mL of dry THE at room temperature in the dark was added 180 mg (1.05 mmol) of recrystallized N-bromosuccinimide. The reaction mixture was stirred under argon for 1 h at room temperature. The solvent was concentrated under diminished pressure and the resulting residue was purified by flash chromatography on a silica gel column (15×2 cm). Elution with 95:1 to 8:2 hexane/EtOAc afforded compound 17 as a colorless solid: yield 249 mg (87%); mp 90° C.; silica gel TLC $R_f$ 0.15 (9:1 hexane/EtOAc); $^1$H NMR ($CDCl_3$) δ 2.10-2.24 (m, 4H), 2.28 (s, 3H), 3.97 (t, 4H, J=7.5 Hz), 4.22 (t, 4H, J=7.5 Hz); $^{13}$C NMR ($CDCl_3$) δ 16.0, 16.8, 24.6, 50.2, 52.6, 90.5, 160.1, 161.0 and 164.2; mass spectrum (APCI), m/z 283.0562 $(M+H)^+$ ($C_{11}H_{16}{}^{79}BrN_4$ requires m/z 283.0558) and m/z 285.0548 $(M+H)^+$ ($C_{11}H_{16}{}^{81}BrN_4$ requires m/z 2853.0538).

Step 3. Synthesis of 2,4-Di-(azetidin-1-yl)-6-methylpyrimidin-5-ol (4a)

A stirred solution containing 100 mg (0.35 mmol) of 17 in 4 mL of freshly distilled THE was cooled to −78° C. under argon for 10 min. To the resulting suspension was added 240 μL (0.38 mmol) of 1.6 M n-BuLi in hexane and the reaction mixture was stirred at −78° C. for 1 h. Then 75.0 μL (0.70 mmol) of trimethyl borate was added slowly and the reaction mixture was maintained at 0° C. for an additional hour. A solution of 200 μL of $H_2O_2$ (30% v/v) was then added and the reaction was allowed to warm to room temperature and stirred for 30 min. The reaction mixture was diluted by the addition of 30 mL of satd aq $NH_4Cl$ and extracted with two 15-mL portions of $CH_2Cl_2$. The combined organic phase was dried over $MgSO_4$ and concentrated under diminished pressure. The residue was purified by flash chromatography on a silica gel column (15×1 cm). Elution with 100% $CH_2Cl_2$ to 9:1, and then 1:1 $CH_2Cl_2$/EtOAc afforded compound 4a as a colorless solid: yield 51 mg (66%); mp 147° C.; silica gel TLC $R_f$ 0.15 (1:1 $CH_2Cl_2$/EtOAc); $^1$H NMR (DMSO-d6) δ 2.05 (s, 3H), 2.10-2.24 (m, 4H), 3.81 (t, 4H, J=7.5 Hz), 4.06 (t, 4H, J=7.5 Hz) and 7.30 (s, 1H); $^{13}$C NMR ($CDCl_3$) δ 15.6, 16.7, 18.2, 50.3, 51.6, 127.9, 151.8, 156.9 and 158.0; mass spectrum (APCI), m/z 221.1406 $(M+H)^+$ ($C_{11}H_{17}N_4O$ requires m/z 221.1402).

Example 11. Synthesis of 2,4-Di-(azetidin-1-yl)-6-tetradecylpyrimidin-5-ol (4b)

Step 1. Synthesis of 2,4-Di-(azetidin-1-yl)-6-tetradecylpyrimidine (18a)

A stirred solution containing 204 mg (1.00 mmol) of 16 in 10 mL of freshly distilled THE was cooled to −78° C. and maintained under argon. After 15 min, 625 μL (1.00 mmol) of 1.6 M n-BuLi in hexane was added dropwise and the reaction mixture was stirred at −78° C. for 1 h. A solution of 276 mg (0.69 mmol) of 1-bromotridecane in 500 μL of distilled THE was then added dropwise and the reaction mixture was stirred at 0° C. for 1 h. The reaction was quenched by the addition of 50 mL of satd aq $NH_4Cl$ and extracted with two 30-mL portions of $CH_2Cl_2$. The combined organic phase was dried over $MgSO_4$ and concentrated under diminished pressure. The residue was purified by flash chromatography on a silica gel column (15×3 cm). Elution with 9:1 to 1:1 hexane/EtOAc afforded compound 18a as a colorless solid: yield 378 mg (98%); mp 64° C.; silica gel TLC $R_f$ 0.2 (2:1 hexane/EtOAc); $^1H$ NMR ($CDCl_3$) δ 0.87 (t, 3H, J=6.9 Hz), 1.12-1.35 (m, 22H), 1.65 (qt, 2H, J=7.6 Hz), 2.24 (qt, 2H, J=7.6 Hz), 2.32 (qt, 2H, J=7.6 Hz), 2.41 (m, 2H), 3.98 (t, 4H, J=7.6 Hz), 4.05 (t, 4H, J=7.6 Hz) and 5.39 (s, 1H); $^{13}C$ NMR ($CDCl_3$) δ 14.2, 16.3, 16.8, 22.8, 28.9, 29.5, 29.55, 29.64, 29.7, 29.76, 29.79, 32.0, 38.1, 49.8, 50.3, 90.06, 90.11, 163.7, 164.6 and 169.4; mass spectrum (APCI), m/z 387.3485 $(M+H)^+$ ($C_{24}H_{43}N_4$ requires m/z 387.3488).

Step 2. Synthesis of 2,4-Di-(azetidin-1-yl)-5-bromo-6-tetradecylpyrimidine (19a)

To a stirred solution containing 195 mg (0.50 mmol) of 18a in 7 mL of dry THE at room temperature in the dark was added 91.0 mg (0.52 mmol) of recrystallized N-bromosuccinimide. The reaction mixture was stirred under argon for 1 h at room temperature. The solvent was concentrated under diminished pressure and the resulting residue was purified by flash chromatography on a silica gel column (15×2 cm). Elution with 99:1 to 95:5 hexane/EtOAc afforded compound 19a as a colorless solid: yield 232 mg (98%); mp 58° C.; silica gel TLC $R_f$ 0.45 (9:1 hexane/EtOAc); $^1H$ NMR ($CDCl_3$) δ 0.88 (t, 3H, J=6.9 Hz), 1.19-1.39 (m, 22H), 1.62 (qt, 2H, J=7.5 Hz), 2.15-2.30 (m, 4H), 2.62 (m, 2H), 4.02 (t, 4H, J=7.5 Hz) and 4.28 (t, 4H, J=7.5 Hz); $^{13}C$ NMR ($CDCl_3$) δ 14.2, 16.22, 16.26, 22.8, 28.1, 29.5, 29.62, 29.64, 29.72, 29.80, 29.82, 32.1, 37.1, 50.4, 52.9, 90.6, 160.7, 161.5 and 168.0; mass spectrum (APCI), m/z 465.2584 $(M+H)^+$ ($C_{24}H_{42}{}^{79}BrN_4$ requires m/z 465.2593) and m/z 467.2568 $(M+H)^+$ ($C_{24}H_{42}{}^{81}BrN_4$ requires m/z 467.2572).

Step 3. Synthesis of 2,4-Di-(azetidin-1-yl)-6-tetradecylpyrimidin-5-ol (4b)

A stirred solution containing 150 mg (0.32 mmol) of 19a in 4 mL of freshly distilled THE was cooled to −78° C. under argon for 10 min. To the resulting suspension was added 210 μL (0.33 mmol) of 1.6 M n-BuLi in hexane and the resulting reaction mixture was stirred at −78° C. for 1 h. Then 71.0 μL (0.64 mmol) of trimethyl borate was added slowly and the reaction mixture was stirred at 0° C. for an additional hour.

A solution of 400 μL of $H_2O_2$ (30% v/v) was then added and the reaction mixture was allowed to warm to room temperature and was stirred for 30 min. The reaction mixture was diluted by the addition of 50 mL of satd aq $NH_4Cl$ and extracted with two 20-mL portions of $CH_2Cl_2$. The combined organic phase was dried over $MgSO_4$ and concentrated under diminished pressure. The residue was purified by flash chromatography on a silica gel column (15×1 cm). Elution with 95:5 to 9:1, and then 1:2 hexane/EtOAc afforded compound 4b as a colorless solid: yield 89 mg (53%); mp 65° C.; silica gel TLC $R_f$ 0.15 (1:1 hexane/EtOAc); $^1H$ NMR (3:1 $CD_3CN/CD_2Cl_2$) δ 0.76 (s, 3H), 1.00-1.25 (m, 22H), 1.42-1.52 (br s, 2H), 2.02-2.18 (m, 4H), 2.39 (br s, 2H), 3.79 (br s, 4H), 4.02 (br s, 4H) and 6.18 (br s, 1H); $^{13}C$ NMR (3:1 $CD_3CN/CD_2Cl_2$) δ 14.3, 16.5, 17.7, 23.2, 25.5, 28.5, 28.7, 29.9, 30.2, 30.26, 30.29, 30.36, 30.44, 31.6, 32.5, 43.9, 51.1, 51.4, 52.5, 128.5, 150.9, 158.1 and 159.6; mass spectrum (APCI), m/z 403.3435 $(M+H)^+$ ($C_{24}H_{43}N_4O$ requires m/z 403.3437).

Example 12. Synthesis of 2,4-Di-(Azetidin-1-yl)-6-hexadecylpyrimidin-5-ol (4c)

Step 1. Synthesis of 2,4-Di-(azetidin-1-yl)-6-hexadecylpyrimidine (18b)

A stirred solution containing 205 mg (1.00 mmol) of 16 in 10 mL of freshly distilled THE was cooled to −78° C. under argon. After 15 min, 625 μL (1.00 mmol) of 1.6 M n-BuLi in hexane was added dropwise and the resulting reaction mixture was stirred at −78° C. for 1 h. A solution of 305 mg (1.05 mmol) of 1-bromopentadecane in 500 μL of distilled THF was then added dropwise and the reaction was stirred at 0° C. for 1 h. The reaction was quenched by adding 50 mL of satd aq $NH_4Cl$ and extracted with two 30-mL portions of $CH_2Cl_2$. The combined organic phase was dried over $MgSO_4$ and concentrated under diminished pressure. The residue was purified by flash chromatography on a silica gel column (15×3 cm). Elution with 9:1 to 1:1 hexane/EtOAc afforded compound 18b as a colorless solid: yield 337 mg (81%); mp 63° C.; silica gel TLC $R_f$ 0.2 (2:1 hexane/EtOAc); $^1H$ NMR ($CDCl_3$) δ 0.86 (t, 3H, J=6.9 Hz), 1.15-1.35 (m, 26H), 1.60 (qt, 2H, J=7.6 Hz), 2.22 (qt, 2H, J=7.5 Hz), 2.30 (qt, 2H, J=7.5 Hz), 2.40 (m, 2H), 3.97 (t, 4H, J=7.5 Hz), 4.04 (t, 4H, J=7.5 Hz) and 5.38 (s, 1H); $^{13}C$ NMR ($CDCl_3$) δ 14.1, 16.2, 16.7, 22.7, 28.8, 29.4, 29.5, 29.6, 29.64, 29.71, 29.73, 29.75, 32.0, 38.0, 49.7, 50.2, 90.0, 163.7, 164.5 and 169.4; mass spectrum (APCI), m/z 415.3807 $(M+H)^+$ ($C_{26}H_{47}N_4$ requires m/z 415.3801).

Step 2. Synthesis of 2,4-Di-(azetidin-1-yl)-5-bromo-6-hexadecylpyrimidine (19b)

To a stirred solution containing 267 mg (0.64 mmol) of 18b in 7 mL of dry THE at room temperature in the dark was added 120 mg (0.67 mmol) of recrystallized N-Bromosuccinimide. The reaction mixture was stirred under argon for 1 h at room temperature. The solvent was removed under reduced pressure and the resulting residue was purified by flash chromatography on a silica gel column (15×2 cm). Elution with 99:1 to 95:5 hexane/EtOAc to afford compound 19b as a colorless solid: yield 289 mg (91%); mp 56° C.; silica gel TLC $R_f$ 0.45 (9:1 hexane/EtOAc); $^1H$ NMR ($CDCl_3$) δ 0.88 (t, 3H, J=7.0 Hz), 1.16-1.37 (m, 26H), 1.62 (qt, 2H, J=7.6 Hz), 2.16-2.29 (m, 4H), 2.62 (m, 2H), 4.02 (t, 4H, J=7.6 Hz) and 4.28 (t, 4H, J=7.6 Hz); $^{13}C$ NMR ($CDCl_3$) δ 14.2, 16.22, 16.26, 22.8, 28.1, 29.5, 29.62, 29.64, 29.73, 29.80, 29.84, 32.1, 37.1, 50.4, 52.9, 90.6, 160.7, 161.5 and 168.0; HRMS (APCI+), m/z 493.2916 $(M+H)^+$ ($C_{26}H_{46}{}^{79}BrN_4$ requires m/z 493.2906). m/z 495.2871 $(M+H)^+$ ($C_{26}H_{46}{}^{81}BrN_4$ requires m/z 495.2885).

Step 3. Synthesis of 2,4-Di-(Azetidin-1-yl)-6-hexadecylpyrimidin-5-ol (4c)

A stirred solution containing 215 mg (0.43 mmol) of 19b in 5 mL of freshly distilled THF was cooled to −78° C. under argon for 10 min. To the resulting suspension was added 280 µL (0.45 mmol) of 1.6 M n-BuLi in hexane and the resulting reaction mixture was stirred at −78° C. for 1 h. Then 100 µL (0.90 mmol) of trimethyl borate was added slowly and the reaction mixture was stirred at 0° C. for an additional hour. A solution of 400 µL of $H_2O_2$ (30% v/v) was then added and the reaction mixture was allowed to warm to room temperature and stirred for 30 min. The reaction mixture was diluted by the addition of 50 mL satd aq $NH_4Cl$ and then extracted with two 20-mL portions of $CH_2Cl_2$. The combined organic phase was dried over $MgSO_4$ and concentrated under diminished pressure. The residue was purified by flash chromatography on a silica gel column (15×1 cm). Elution with 95:5 to 9:1, and then 1:2 hexane/EtOAc afforded compound 4c as a colorless solid: yield 124 mg (66%); mp 65° C.; silica gel TLC $R_f$ 0.15 (1:1 hexane/EtOAc); $^1H$ NMR (3:1 $CD_3CN/CD_2Cl_2$) δ 0.76 (s, 3H), 1.00-1.25 (m, 26H), 1.42-1.52 (br s, 2H), 2.00-2.18 (m, 4H), 2.39 (br s, 2H), 3.79 (br s, 4H), 4.02 (br s, 4H) and 6.00 (br s, 1H); mass spectrum (APCI), m/z 431.3741 $(M+H)^+$ ($C_{26}H_{47}N_4O$ requires m/z 431.3750). Due to poor solubility of the product, no $^{13}C$ NMR spectrum of reasonable quality could be obtained.

Biochemical and Biological Evaluation

Cell Lines and Culture Conditions

Human mitochondrial disease cell lines, Friedreich's ataxia lymphocytes (GM15850), and Leigh's syndrome lymphocytes (GM13740) were obtained from Coriell Cell Repositories (Camden, NJ). Lymphocytes were cultured in RPMI-1640 medium (Gibco, Life Technologies, Grand Island, NY) with 15% fetal calf serum, 2 mM glutamine (HyClone, South Logan, UT) and 1% penicillin-streptomycin antibiotic supplement (Cellgro, Manassas, VA). Cells were passaged every other day to maintain them in log phase growth and kept at a nominal concentration of 5-10×$10^5$ cell/mL. A $CoQ_{10}$ deficient lymphocyte cell line (GM17932) was obtained from Coriell Cell Repositories. A nutrient sensitized screening strategy to identify $CoQ_{10}$ analogues that function within the mitochondrial respiratory chain was used by growing the $CoQ_{10}$-deficient lymphocyte in galactose containing media to force energy production predominantly through oxidative phosphorylation rather than glycolysis (Goldschmidt, R., et al. *Bioorg. Med. Chem.* 2013, 21, 969; Khdour, O. M., et al. *ACS Med. Chem. Lett.* 2013, 4, 724; Ehrenberg, B., et al. *Biophys. J.* 1988, 53, 785; Aguer, C., et al. *PLoS One* 2011, 6, 28536; and Arce, P. M., et al. *Bioorg. Med. Chem.* 2012, 20, 5188). The lymphocytes were cultured in RPMI 1640 glucose free medium (Gibco, Grand Island, NY) supplemented with 25 mM galactose, 2 mM glutamine and 1% penicillin-streptomycin, and 10% dialyzed fetal bovine serum (FBS) (<0.5 µg/mL) (Gemini Bio-Product, West Sacramento, CA).

Example 13. NADH Oxidase Activity

A small scale preparation of bovine heart mitochondria is prepared as described by Smith (Smith, A. L. *Methods Enzymol.* 1967, 10, 81). Bovine heart submitochondrial particles (SMPs) are prepared as described by Matsuno-Yagi and stored in a buffer containing 0.25 M sucrose and 10 mM Tris-HCl, pH 7.4, at −80° C. (Matsuno-Yagi, A., et al. *J. Biol. Chem.* 1985, 260, 11424). SMPs are diluted to 0.5 mg/mL. Mitochondrial complexes I, III, and IV activity are assayed at 30° C. and monitored spectrophotometrically using a Beckman Coulter DU-530 (340 nm, e=6.22 $mM^{-1}$ $cm^{-1}$). NADH oxidase activity is determined in 50 mM Hepes buffer containing 5 mM $MgCl_2$, pH 7.5, in a total volume of 2.5 mL. The final mitochondrial protein concentration was 30 µg/mL. The initial rates of NADH oxidation were calculated from the linear portion of the traces. Data are reported as the mean of three independent experiments each run in triplicate.

Example 14. Lipid Peroxidation Assay

Lipid peroxidation was measured by a quantitative FACS assay using the oxidation-sensitive fatty acid probe $C_{11}$-BODIPY$^{581/591}$ (Molecular Probe) as described in art (Goldschmidt, R., et al. *Bioorg. Med. Chem.* 2013, 21, 969; Khdour, 0. M., et al. *ACS Med. Chem. Lett.* 2013, 4, 724; and Arce, P. M., et al. *Bioorg. Med. Chem.* 2012, 20, 5188). The degree of probe oxidation was followed using flow cytometry. Briefly, FRDA lymphocytes (5×$10^5$ cell/mL) were plated (1 mL in 24-well plates), treated with the test compounds and incubated at 37° C. for 16 h in a humidified atmosphere containing 5% $CO_2$ in air. The following day, cells were treated with 1 µM of $C_{11}$-BODIPY$^{581/591}$ probe in phenol red-free media and incubated at 37° C. in the dark for 30 min. Oxidative stress was induced with 5 mM DEM in phenol red-free RPMI-1640 media for 120 min. Cells were collected by centrifugation at 300×g for 3 min and then washed with phosphate buffered saline (PBS). Cells were resuspended in phosphate buffered saline and were analyzed immediately by FACS (C6 Accuri, BD Biosciences, San Jose, CA), using a 488 nm excitation laser and the FL1-H channel 530±15 nm emission filter. The generation of lipid peroxide was detected as a result of the oxidation of the polyunsaturated butadienyl portion of the dye, resulting in a shift of the fluorescence emission peak from red to green. In each analysis, 10,000 events were recorded after cell debris were electronically gated out. Data are reported as means S.E.M. (n=3). Results were expressed as a percentage of the median mean fluorescence intensity of $C_{11}$-BODIPY-green relative to the treated control (DEM).

Figure 2:
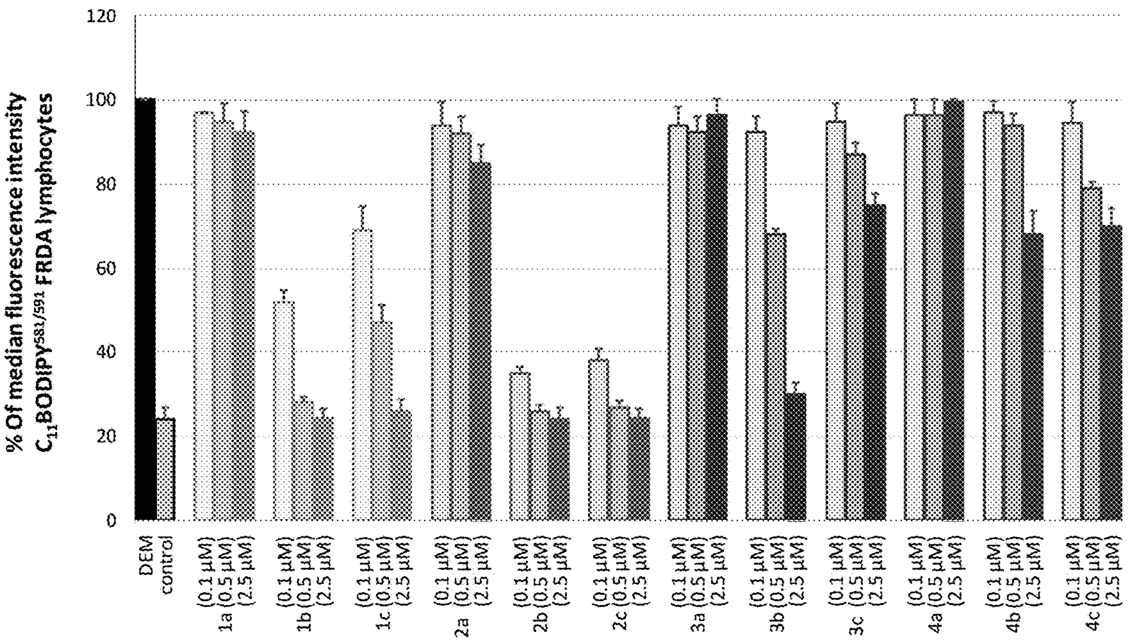
FIG. 2 shows Lipid peroxidation in FRDA lymphocytes cells depleted of glutathione by utilizing the oxidation-sensitive fatty acid probe $C_{11}$-BODIPY$^{581/591}$ and fluorescence activated cell sorting (FACS). The bar graph represents the percentage of the median mean fluorescence intensity of $C_{11}$-BODIPY-green fluorescence relative to a treated control is shown. Data are expressed as the mean±SEM (n=3).

The lipophilic fluorophore changes its fluorescence from red to green when it interacts with peroxyradicals and a measurement using FACS of intracellular lipid peroxidation, was determined by increasing the median mean fluorescence intensity of $C_{11}$-BODIPY-green relative to the untreated control. The results presented in the FIG. 2 show several important findings. First it appears that the combination of an alkoxy and an alkylamino moiety is necessary to afford good suppression of lipid peroxidation, considering that none of the dialkoxy (3a-c) or the dialkylamino (4a-c) compounds afforded good suppression. One might consider compound 3b as slightly efficient, but this was only observed at high concentration. On the contrary, compounds 1b-c and 2b-c efficiently suppressed lipid peroxidation, especially at high concentration, and there was differentiation between the two regioisomers at low concentration, as 2b was significantly more efficient than 1b at 0.1 µM concentration, just as 2c was better than 1c. The localization of the alkoxy moiety in position 2 looks more efficient in this case. Finally, the presence of a hydrophobic side chain is confirmed to be essential as no activity was observed for any redox core (1a-4a).

Example 15. Reactive Oxygen Species (ROS) Assay

Quantitative analysis of intracellular ROS levels in FRDA lymphocytes, challenged with 5 mM diethyl maleate (DEM) in presence or absence of the test compounds, was obtained by FACS analysis using a dichlorodihydrofluorescein diacetate probe (DCFH-DA), as described in art (Goldschmidt, R., et al. *Bioorg. Med Chem.* 2013, 21, 969; Arce, P. M., et al. *Bioorg. Med Chem.* 2012, 20, 5188; Arce, P. M., et al. *ACS Med Chem. Lett.* 2011, 2, 608; Khdour, O. M., et al. *Pharm. Res.* 2011, 28, 2896; Lu, J., et al. *Bioorg. Med Chem.* 2010, 18, 7628; and Cai, X., et al. *Bioorg. Med Chem.* 2012, 20, 3584). Briefly, 1 mL of FRDA lymphocytes ($5\times10^5$ cells) was plated in a 24-well plate, treated with the test compounds and incubated at 37° C. for 16 hours in a humidified atmosphere containing 5% $CO_2$ in air. Cells were treated with 5 mM diethyl maleate (DEM) for 80 minutes, collected by centrifugation at 300×g for 3 minutes and then washed with phosphate buffered saline (Life Technologies). Cells were resuspended in PBS containing 20 mM glucose and incubated at 37° C. in the dark for 25 minutes with 10 μM DCFH-DA. Cells were collected by centrifugation at 300 g for 3 minutes and then washed with PBS. The samples were analyzed immediately by flow cytometry (C6 Accuri, BD Biosciences, San Jose, CA), using a 488 nm excitation laser and the FL1-H channel 530±15 nm emission filter. The generation of ROS, mainly peroxides, was detected as a result of the oxidation of DCFH. In each analysis, 10,000 events were recorded after cell debris was electronically gated out. Results obtained were verified by running duplicates and repeating experiments in three independent runs. Results were expressed as a percentage of ROS scavenging activity. Results were expressed as a percentage of the median mean fluorescence intensity of DCF relative to the treated control.

Figure 3:
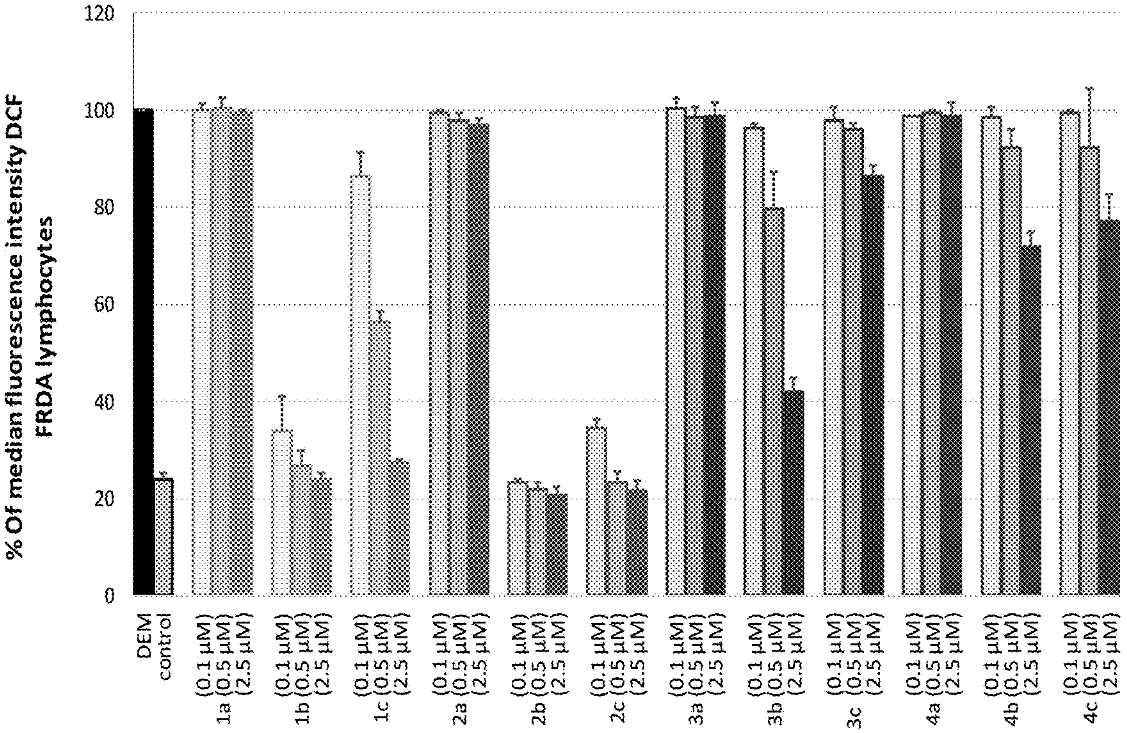
FIG. 3 shows flow cytometric analysis of ROS in FRDA lymphocyte cells pre-treated with compounds 1a-c, 2a-c, 3a-c and 4a-c at 0.1 μM, 0.5 μM and 2.5 μM concentrations for 16 hours, and then treated with diethyl maleate (DEM) for 80 minutes to induce the production of ROS. The cells were stained with 2, 7-dichlorodihydrofluorescein diacetate (DCFH-DA) for 15 minutes prior to analysis. The samples were analyzed immediately by flow cytometry (C6 Accuri, BD Biosciences, San Jose, CA). The bar graph represents the percentage of the median mean fluorescence intensity of DCF fluorescence relative to a DEM-treated control. Data shown represent the mean±SEM of two different experiments run as duplicates.

FIG. 3 presents the results obtained in FRDA lymphocyte cells for all the quenchers tested including the redox cores. The behaviors observed in this case are similar to the results observed for lipid peroxidation. While compound 3b appeared to be efficient at high concentration, as soon as the concentration was decreased to 0.5 μM, the protection given by the dialkoxy analogues (3a-c) or dialkylamino analogues (4a-c) was minimal. Also, the association of an alkylamino and an alkoxy groups was obviously a determinant of good efficiency for all the compounds at high concentration even if a difference in favor of the compounds 2b-c was observed at low concentration. This confirms the importance of having an alkoxy and an alkylamino moiety on the pyrimidinol scaffold bearing a hydrophobic side chain. The trend in which the isomer with the alkylamino group in position 6 looks more efficient that in position 2 is also confirmed by this test.

Example 16. Preservation of Mitochondrial Membrane Potential (Δψm)

Figure 4:
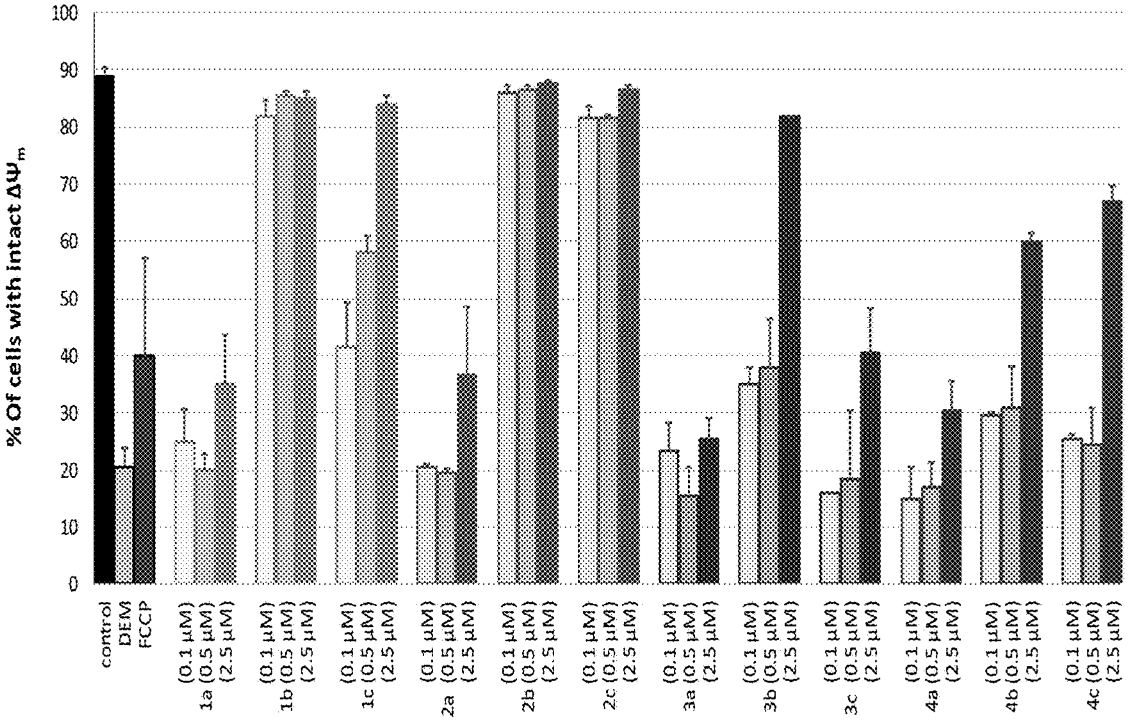
FIG. 4 shows representative flow cytometric two-dimensional color density dot plot analyses of the ability of compounds 1a-c, 2a-c, 3a-c and 4a-c to maintain mitochondrial membrane potential ($\Delta\psi_m$) in DEM-treated FRDA lymphocytes cells stained with 250 nM TMRM and analyzed using the FL2-H channel as described in the Example. A total of 10,000 events were recorded for each sample and analyzed using C6 Accuri software (BD Biosciences). The bar graph represents the percentage of the cells with intact $\Delta\psi_m$. Data are expressed as means±S.E.M. of two independent experiments run in duplicate.

Mitochondrial membrane potential of FRDA lymphocytes was assessed using the fluorescence probe Mitotracker TMRM (tetramethylrhodamine methyl ester; Molecular Probes, Portland, OR) as described in art (Goldschmidt, R., et al. *Bioorg. Med Chem.* 2013, 21, 969; Khdour, O. M., et al. *ACS Med Chem. Lett.* 2013, 4, 724; Arce, P. M., et al. *Bioorg. Med Chem.* 2012, 20, 5188; Lu, J., et al. *Bioorg. Med Chem.* 2010, 18, 7628; and Cai, X., et al. *Bioorg. Med Chem.* 2012, 20, 3584). TMRM is a lipophilic potentiometric dye which partitions between the mitochondria and cytosol in proportion to the negative membrane potential across the inner mitochondrial membrane, in accordance with the Nernst equation (Ehrenberg, B., et al. *Biophys. J.* 1988, 53, 785). Therefore, the accumulation of dye in the mitochondria and the intensity of the signal is a direct function of mitochondrial membrane potential. Mitochondrial depolarization then causes the redistribution of dye from mitochondria into the cytosol, causing a change in signal intensity. The detection of mitochondrial depolarization using TMRM was accomplished by flow cytometry as described in art (Goldschmidt, R., et al. *Bioorg. Med. Chem.* 2013, 21, 969; Khdour, O. M., et al. *ACS Med. Chem. Lett.* 2013, 4, 724; and Arce, P. M., et al. *Bioorg. Med. Chem.* 2012, 20, 5188). Briefly, FRDA lymphocytes cells ($5\times10^5$ cells) were pre-treated with or without the test compounds for 16 hours. The cells were treated with 5 mM DEM for 120 minutes, collected by centrifugation at 300×g for 3 minutes and washed with phosphate buffered saline. The cells were resuspended in PBS containing 20 mM glucose and incubated at 37° C. in the dark for 15 minutes with 250 nM TMRM. Cells were collected by centrifugation at 300×g for 3 minutes and washed with phosphate buffered saline. Cells were resuspended in phosphate buffered saline supplemented with 20 mM glucose and were analyzed immediately by FACS (C6 Accuri, BD Biosciences, San Jose, CA), using a 488 nm excitation laser and the FL2-H channel. For each analysis 10,000 events were recorded and the percentage of cells exhibiting a high level of TMRM uptake, which reflects normal mitochondrial membrane potential, was determined and analyzed using C6 Accuri software (BD Biosciences). The results obtained were verified in three independent experiments. FCCP (carbonyl cyanidep-trifluoromethoxyphenylhydrazone), a mitochondrial uncoupler, was used to produce a negative control. The results were verified by repeating the experiments in duplicate (FIG. 4).

Example 17. Cytoprotection (FACS Analysis Live/Dead® Viability/Cytotoxicity Assay)

The cytoprotection conferred by the representative compounds was determined in FRDA lymphocytes by using a simultaneous staining with a two-color fluorescence FACS assay, the Live/Dead® Viability/Cytotoxicity Kit (Molecular Probes). This assay is used to measure two recognized parameters of cell viability, intracellular esterase activity and plasma integrity. The membrane-impermeant DNA dye ethidium homodimer-1 (EthD-1) was used to identify dead cells whose plasma membrane integrity was disrupted. The membrane-permeant dye calcein-AM was used to label live cells. It penetrates into the cells, where it is metabolized by cytoplasmic esterases and becomes a fluorescent but membrane-impermeant probe which is retained in viable cells. Briefly, FRDA lymphocyte cells were seeded at a density of $5\times10^5$ cells/mL and treated with different concentrations of the test compounds. Cells were incubated at 37° C. in a humidified atmosphere of 5% $CO_2$ in air for 16 hours. Oxidative stress was then induced by incubation with 5 mM DEM for 6 hours, followed by evaluation of cytoprotection. Cells were collected by centrifugation at 300×g for 3 minutes and washed with phosphate buffered saline. Cells were resuspended in phosphate buffered saline containing 25 mM galactose. The cell suspension was stained with 0.1 μM calcein AM and 0.1 μM EthD-1 and incubated in the dark at 37° C. for 15 minutes. Cells were collected by centrifugation at 300×g for 3 minutes and then washed with PBS. The samples were analyzed immediately by flow cytometry (C6 Accuri, BD Biosciences, San Jose, CA), using a 488 nm excitation laser and the FL1-H channel 530±15 nm emission filter and the FL2-H channel 585±15 nm. For each analysis 10,000 events were recorded and analyzed using C6 Accuri software (BD Biosciences). Cytoprotection by the test compounds was assessed with respect to the untreated controls. Cells not treated with DEM had >90% cell viability whereas DEM treatment reduced cell viability to <20%. The cell viability was expressed relative to the vehicle control (DMSO only) group (n=3).

Figure 5:
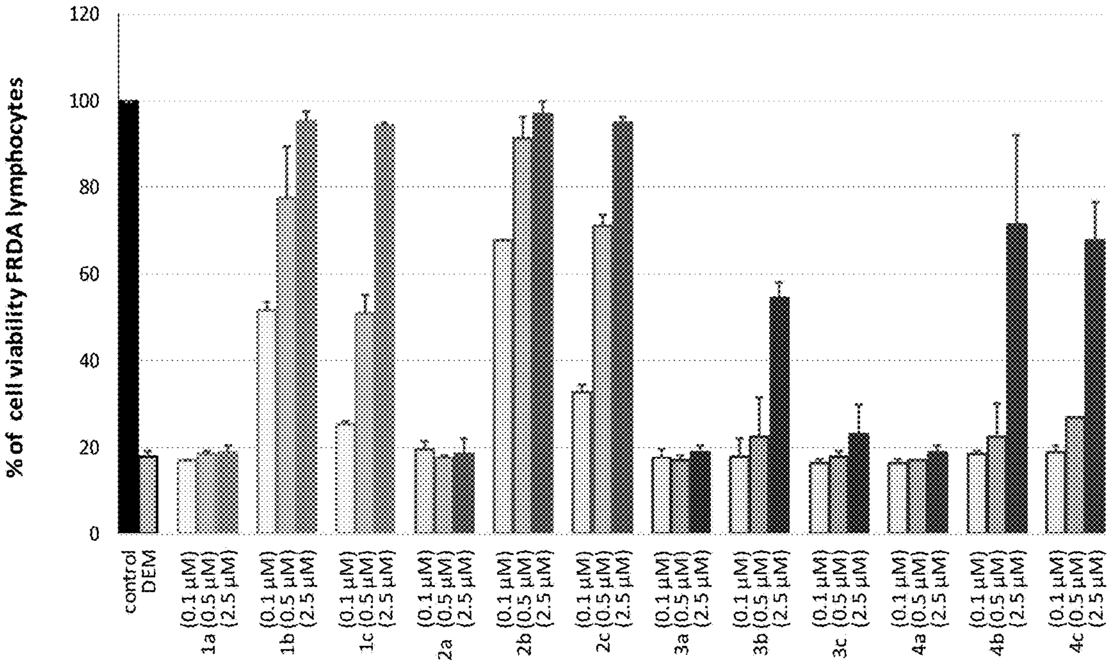
FIG. 5 shows cell viability of Friedreich's ataxia lymphocytes following pretreatment with the test compounds for 16 hours and then treatment with DEM (5 mM) for 6 hours to induce oxidative stress. Flow cytometric determination of cell viability by fluorescence labeling was used employing calcein acetoxy-methyl-ester and ethidium homodimer-1 (EthD-1) as live and dead cell stains. Cell viability was expressed as the percentage of cells relative to control. Results are an average of two independents trials run in duplicate.

The trend described in Examples 14-16 was found to be general as the same results were obtained by analyzing the capability of these molecules to preserve mitochondrial membrane potential (FIG. 4) or during the experiments to evaluate the cytoprotective effect of these quenchers (FIG. 5). All of these experiments lead to the same conclusion: the association of an alkoxy and an alkylamino moiety is essential to confer good cytoprotection, protection against lipid peroxidation or ROS over expression, and to preserve mitochondrial membrane potential. The additional information given by these tests is that the specific regioisomer is also important as the alkoxy group localized at position 2 looks much more efficient and enables the use of these MRQs at lower concentration while maintaining their biological properties.

Example 18. Cellular ATP Concentration Assay $CoQ_{10}$ deficient lymphocytes ($2\times10^5$ cell/mL) were plated (1 mL in 24-well plates) in glucose-free media supplemented with galactose and treated with the test compounds at final concentrations of 5, 10 and 25 μM, and then incubated at 37° C. for 48 h in a humidified atmosphere containing 5% $CO_2$ in air. Wells were mixed and cells in each well were transferred (100 μL) to 96-well microtiter black-walled cell culture plates (Costar, Corning, NY). The total intracellular ATP level was measured in a luminator (Clarity™ luminescence microplate reader) using an ATP Bioluminescence Assay Kit (ViaLight-Plus ATP monitoring reagent kit, Lonza, Walkersville, MD) following the manufacturer's protocol. The total ATP level was expressed as a percentage of untreated control. Data are reported as the mean of at least three independent runs.

In the present study, analogues 1a-c, 2a-c, 3a-c and 4a-c were evaluated for their ability to enhance ATP levels. Table 1 presents the results obtained during this experiment and leads to a different conclusion. First, when the dialkoxy compounds (3a-c) were not efficient in the previous assays, they support ATP production even at high concentration (20 μM), at which inhibition usually starts to be observed. Unfortunately, this time again, the combination of two alkylamino moieties as in the compounds 4a-c is obviously harmful, resulting in complete inhibition at 20 μM concentration and around 50% inhibition for compounds 4b-c at 5 μM concentration. It may be noted that this effect seems less obvious with the redox core 4a. All of the other compounds support ATP production except compound 2b but only at high concentration. We also note that the difference between the compounds 1a-c and 2a-c is less obvious in this case, with comparable efficiencies obtained at low concentration.

TABLE 1

Total ATP concentration in FRDA lymphocytes following incubation with compounds 1a-c, 2a-c, 3a-c and 4a-c for 48 h[a]

| Compound | Total ATP level (% control) FRDA lymphocytes 1 μM | 5 μM | 20 μM |
|---|---|---|---|
| Untreated control | 100 | 100 | 100 |
| 1a | 100 ± 1 | 98 ± 1 | 96 ± 2 |
| 1b | 105 ± 3 | 102 ± 1 | 94 ± 2 |
| 1c | 100 ± 1 | 114 ± 3 | 103 ± 2 |
| 2a | 101 ± 1 | 99 ± 3 | 96 ± 3 |
| 2b | 109 ± 3 | 105 ± 2 | 54 ± 6 |
| 2c | 102 ± 2 | 110 ± 4 | 99 ± 2 |
| 3a | 101 ± 1 | 99 ± 2 | 97 ± 3 |
| 3b | 99 ± 1 | 98 ± 2 | 94 ± 2 |
| 3c | 98 ± 2 | 102 ± 2 | 96 ± 2 |
| 4a | 101 ± 2 | 101 ± 2 | 85 ± 9 |
| 4b | 86 ± 3 | 46 ± 7 | 1 ± 0 |
| 4c | 92 ± 1 | 61 ± 9 | 1 ± 2 |

[a]Determined from intracellular ATP levels using the luciferin-luciferase reaction.

Example 19. Microsomal Stability Assay

Liver tissues were diced into small pieces and then washed with isotonic sucrose buffer (0.25 M sucrose, 10 mM Tris-HCl, 0.5 mM EDTA, pH 7.8). The diced tissue was passed through a precooled meat grinder and mixed with three-fold ice cold sucrose buffer supplemented with a mixture of protease inhibitors. The suspension was homogenized in a Waring blender for 25 s at high speed. At this stage, the pH of the suspension was adjusted to 7.4 with 1 M Tris base. The homogenate was centrifuged for 20 min at 1200×g to remove cell debris. The supernatant suspension was homogenized in a tight fitting Teflon-glass Potter-Elvehjem homogenizer and then centrifuged twice at 10,000×g for 20 min, collecting the supernatant each time to remove mitochondria. The floating fat layer was carefully removed by filtering the supernatant through layers of cheesecloth. The supernatant was centrifuged at 150,000×g for 30 min (Beckman-Coulter ultracentrifuge, XL-100K-01, SW 55 Ti rotor). The pellet (microsomal fraction) was suspended in 0.25 M sucrose buffer containing 10 mM Tris-HCl, pH 7.4, with 20% (v/v) glycerol, and centrifuged once more at 150,000×g. The pellet was resuspended in sucrose buffer with 20% (v/v) glycerol. The protein concentration after resuspension was approximately 20 mg/mL, as determined by BCA protein assay (Pierce Chemical) using bovine serum albumin as a standard. Aliquots of microsomal suspensions were stored at −80° C.

In vitro metabolic stability was determined in bovine liver microsomes at a protein concentration of 1 mg/mL in 50 mM phosphate buffer mixture, pH 7.4, containing 5 mM $MgCl_2$ in a final incubation volume of 0.5 mL. Each test compound was added to a final concentration of 25 μM. This mixture was pre-warmed to 37° C. prior to starting the reaction by the addition of β-NADPH to 1 mM final concentration. After incubation for 30 min at 37° C., the reaction was quenched by the addition of 1 mL of propanol, vortexed for 2 min and centrifuged at 15,000×g for 10 min to pellet the precipitated protein. The resulting supernatant was pipetted out and then concentrated under diminished pressure. A parallel incubation of the test compound with deactivated microsomes (quenched immediately with propanol) lacking β-NADPH served as a control and was run for each test agent to detect microsome-independent degradation. The sample was reconstituted in 130 μL MeOH and centrifuged again at 15,000×g for 3 min. The supernatant was removed and 4 μM fluorene was added as an internal standard before HPLC analysis. HPLC analyses were performed on a Zorbax SB-Phenyl reversed phase analytical (150×4.6 mm, 5 m) HPLC column using a mobile phase consisting of MeOH/$H_2O$. A linear gradient of (50:50 MeOH/$H_2O$→100:0 MeOH/$H_2O$) was employed over a period of 14 min at a flow rate of 1 mL/min. Metabolic stability was expressed as percent of control remaining. The experiments were carried out in duplicate to verify the results.

After reversed HPLC quantification, the results were represented in Table 2. The results show a similar stability, around 60-65% for all the compounds, leading to the conclusion that even if the biological properties of these compounds can differ from on analogue to another, the stability remains essentially the same. Only for compound 2b was a significantly better stability observed (77% recovery) but it is clear that the viability of these compounds as MRQs can't be differentiated by their microsome stability, considering the similarity of all these values.

TABLE 2

In vitro microsomal stability of the prepared compounds 1b-c, 2b-c, 3b-c and 4b-c following incubation with bovine liver microsomes. Results expressed as % of compound recovered after reaction with activated microsomes. Microsomal stability values represent means ± SD.

| Compound | Recovery (%) |
|---|---|
| 1b | 63 ± 8 |
| 1c | 65 ± 8 |
| 2b | 77 ± 3 |
| 2c | 63 ± 9 |
| 3b | 72 ± 3 |
| 3c | 60 ± 5 |
| 4b | 63 ± 5 |
| 4c | 62 ± 3 |

Example 20. The following illustrate representative pharmaceutical dosage forms, containing a compound of formula I (compound X), for therapeutic or prophylactic use in humans.

| | mg/tablet |
|---|---|
| (i) Tablet 1 | |
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |
| (ii) Tablet 2 | |
| Compound X= | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
| | 600.0 |

-continued

| | mg/ml |
|---|---|
| (iv) Injection 1 (1 mg/ml) | |
| Compound X= (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |
| (v) Injection 2 (10 mg/ml) | |
| Compound X= (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X= | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of treating mitochondrial disease, neurodegenerative disease, cardiovascular disease, cancer or diabetes in an animal comprising administering to the animal an effective amount of compound of formula I:

formula I

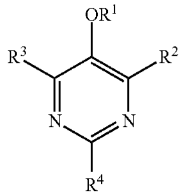

wherein $R^1$ is hydrogen or $C_{1-6}$ alkyl;

$R^2$ is $C_{1-20}$ alkyl, $C_{2-20}$ alkenyl or $C_{2-20}$ alkynyl, and wherein the $C_{1-20}$ alkyl, $C_{2-20}$ alkenyl and $C_{2-20}$ alkynyl are optionally substituted with one or more groups independently selected from —F, —Cl, —Br, —I, —$OR^a$, —$SR^a$, —$N(R^a)_2$, oxo, —$NO_2$ and —CN;

$R^3$ is —$NR^6R^7$;

$R^4$ is —$OR^8$ or —$NR^9R^{10}$;

$R^6$ and $R^7$ taken together with the nitrogen to which they are attached form a 3-10 membered heterocycle that is optionally substituted with one or more groups independently selected from $C_{1-4}$ alkyl, $C_{1-4}$ haloalkyl, —F, —C, —Br, —I, —$OR^e$, —$SR^e$, —$N(R^e)_2$, oxo, —$NO_2$ and —CN;

$R^8$ is $C_{3-10}$ cycloalkyl or $C_{1-8}$ alkyl; wherein $C_{3-10}$ cycloalkyl and $C_{1-8}$ alkyl are optionally substituted with one or more groups independently selected from $C_{1-4}$ alkyl, $C_{1-4}$ haloalkyl, —F, —Cl, —Br, —I, —$OR^f$, —$SR^f$, —$N(R^f)_2$, oxo, —$NO_2$ and —CN;

$R^9$ is $C_{1-6}$ alkyl, $C_{2-6}$ alkenyl or $C_{2-6}$ alkynyl, and wherein the $C_{1-6}$ alkyl, $C_{2-6}$ alkenyl and $C_{2-6}$ alkynyl are optionally substituted with one or more groups independently selected from —F, —Cl, —Br, —I, —$OR^g$, —$SR^g$, —$N(R^g)_2$, oxo, —$NO_2$ and —CN; $R^{10}$ is $C_{1-6}$ alkyl, $C_{2-6}$ alkenyl or $C_{2-6}$ alkynyl, and wherein the $C_{1-6}$ alkyl, $C_{2-6}$ alkenyl and $C_{2-6}$ alkynyl are optionally substituted with one or more groups independently selected from —F, —Cl, —Br, —I, —$OR^h$, —$SR^h$, —$N(R^h)^2$, oxo, —$NO_2$ and —CN; or $R^9$ and $R_{10}$ taken together with the nitrogen to which they are attached form a 3-10 membered heterocycle that is optionally substituted with one or more groups independently selected from $C_{1-4}$ alkyl, $C_{1-4}$ haloalkyl, —F, —Cl, —Br, —I, —$OR^i$, —$SR^i$, —$N(R^i)_2$, oxo, —$NO_2$ and —CN;

each $R^a$ is independently hydrogen or $C_{1-4}$ alkyl; or two $R^a$ taken together with the nitrogen to which they are attached form pyrrolidinyl, piperidinyl, piperazinyl or morpholinyl;

each $R^e$ is independently hydrogen or $C_{1-4}$ alkyl; or two $R^e$ taken together with the nitrogen to which they are attached form pyrrolidinyl, piperidinyl, piperazinyl or morpholinyl;

each $R^f$ is independently hydrogen or $C_{1-4}$ alkyl; or two $R^f$ taken together with the nitrogen to which they are attached form pyrrolidinyl, piperidinyl, piperazinyl or morpholinyl;

each $R^g$ is independently hydrogen or $C_{1-4}$ alkyl; or two $R^g$ taken together with the nitrogen to which they are attached form pyrrolidinyl, piperidinyl, piperazinyl or morpholinyl;

each $R^h$ is independently hydrogen or $C_{1-4}$ alkyl; or two $R^h$ taken together with the nitrogen to which they are attached form pyrrolidinyl, piperidinyl, piperazinyl or morpholinyl; and each $R^i$ is independently hydrogen or $C_{1-4}$ alkyl; or two $R^i$ taken together with the nitrogen to which they are attached form pyrrolidinyl, piperidinyl, piperazinyl or morpholinyl;

or a pharmaceutically acceptable salt thereof.

2. The method of claim 1, wherein $R^2$ is $C_{10-20}$ alkyl.

3. The method of claim 1, wherein $R^2$ is methyl, tetradecyl or hexadecyl.

4. The method of claim 1, wherein $R^6$ and $R^7$ taken together with the nitrogen to which they are attached form

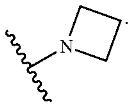

5. The method of claim 1, wherein $R^9$ and $R^{10}$ taken together with the nitrogen to which they are attached form a 3-10 membered heterocycle that is optionally substituted with one or more groups independently selected from $C_{1-4}$ alkyl, $C_{1-4}$ haloalkyl, —F, —Cl, —Br, —I, —$OR^i$, —$SR^i$, —$N(R^i)_2$, oxo, —$NO_2$ and —CN.

6. The method of claim 5, wherein $R^9$ and $R^{10}$ taken together with the nitrogen to which they are attached form

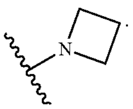

7. The method of claim 1, wherein $R^3$ is —$NR^6R^7$ and $R^4$ is —$OR^8$.

8. The method of claim 1, wherein $R^2$ is $C_{10-20}$ alkyl.

9. The method of claim 1, wherein $R^4$ is

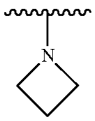
or
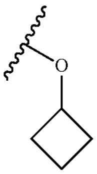
.

10. The method of claim 1, wherein the compound of formula I or the salt thereof is selected from the group consisting of:

2a

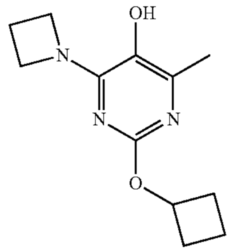

2b

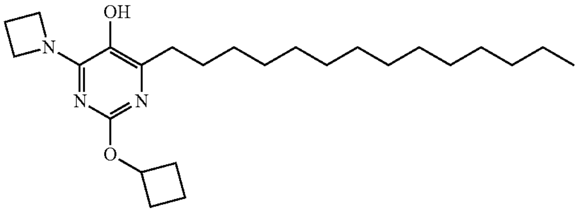

2c

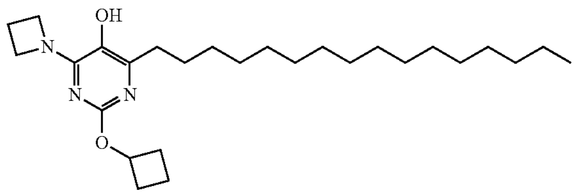

-continued

4a

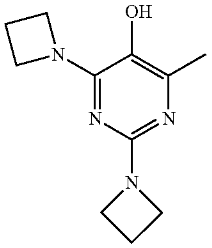

4b

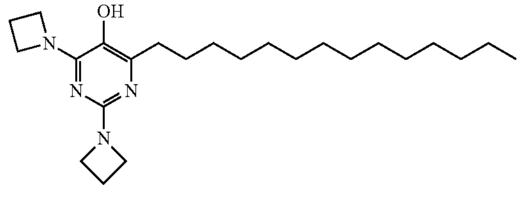

and

4c

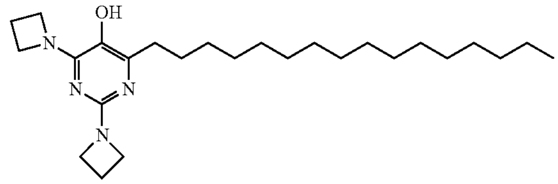

;

and pharmaceutically acceptable salts thereof.

11. The method of claim 1, wherein the compound of formula I or the salt thereof is selected from the group consisting of:

2a

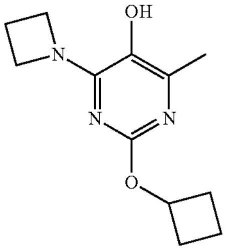

2b

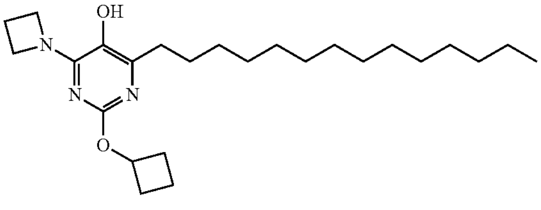

and

2c

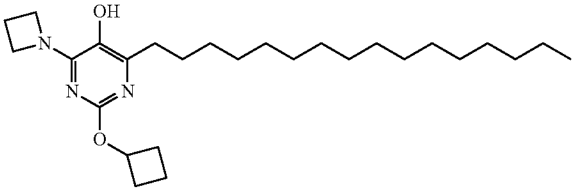

and pharmaceutically acceptable salts thereof.

12. The method of claim 1, wherein the compound of formula I or the salt thereof is:

2b

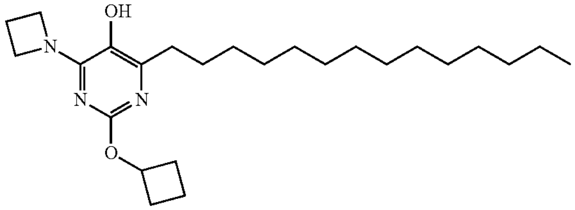

or a pharmaceutically acceptable salt thereof.

13. A method of treating mitochondrial disease, neurodegenerative disease, cardiovascular disease, cancer or diabetes in an animal comprising administering to the animal an effective amount of compound of formula Ib:

formula Ib

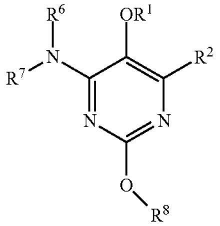

wherein $R^1$ is hydrogen or $C_{1-6}$ alkyl;

$R^2$ is $C_{1-20}$ alkyl, $C_{2-20}$ alkenyl or $C_{2-20}$ alkynyl, and wherein the $C_{1-20}$ alkyl, $C_{2-20}$ alkenyl and $C_{2-20}$ alkynyl are optionally substituted with one or more groups independently selected from —F, —Cl, —Br, —I, —$OR^a$, —$SR^a$, —$N(R^a)_2$, oxo, —$NO_2$ and —CN;

$R^6$ is $C_{1-6}$ alkyl, $C_{2-6}$ alkenyl or $C_{2-6}$ alkynyl, and wherein the $C_{1-6}$ alkyl, $C_{2-6}$ alkenyl and $C_{2-6}$ alkynyl are optionally substituted with one or more groups independently selected from —F, —Cl, —Br, —I, —$OR^c$, —$SR^C$, —$N(R^c)_2$, oxo, —$NO_2$ and —CN; $R^7$ is $C_{1-6}$ alkyl, $C_{2-6}$ alkenyl or $C_{2-6}$ alkynyl, and wherein the $C_{1-6}$ alkyl, $C_{2-6}$ alkenyl and $C_{2-6}$ alkynyl are optionally substituted with one or more groups independently selected from —F, —Cl, —Br, —I, —$OR^d$, —$SR^d$, —$N(R^c)_2$, oxo, —$NO_2$ and —CN; or $R^6$ and $R^7$ taken together with the nitrogen to which they are attached form a 3-10 membered heterocycle that is optionally substituted with one or more groups independently selected from $C_{1-4}$ alkyl, $C_{1-4}$ haloalkyl, —F, —Cl, —Br, —I, —$OR^e$, —$SR^e$, —$N(R^e)_2$, oxo, —$NO_2$ and —CN;

$R^8$ is $C_{3-10}$ cycloalkyl or $C_{1-8}$ alkyl; wherein $C_{3-10}$ cycloalkyl and $C_{1-8}$ alkyl are optionally substituted with one or more groups independently selected from $C_{1-4}$ alkyl, $C_{1-4}$ haloalkyl, —F, —Cl, —Br, —I, —$OR^f$, —$SR^f$, —$N(R^f)_2$, oxo, —$NO_2$ and —CN;

each $R^a$ is independently hydrogen or $C_{1-4}$ alkyl; or two $R^a$ taken together with the nitrogen to which they are attached form pyrrolidinyl, piperidinyl, piperazinyl or morpholinyl;

each $R^c$ is independently hydrogen or $C_{1-4}$ alkyl; or two $R^c$ taken together with the nitrogen to which they are attached form pyrrolidinyl, piperidinyl, piperazinyl or morpholinyl;

each $R^d$ is independently hydrogen or $C_{1-4}$ alkyl; or two $R^d$ taken together with the nitrogen to which they are attached form pyrrolidinyl, piperidinyl, piperazinyl or morpholinyl;

each $R^e$ is independently hydrogen or $C_{1-4}$ alkyl; or two $R^e$ taken together with the nitrogen to which they are attached form pyrrolidinyl, piperidinyl, piperazinyl or morpholinyl;

each $R^f$ is independently hydrogen or $C_{1-4}$ alkyl; or two $R^f$ taken together with the nitrogen to which they are attached form pyrrolidinyl, piperidinyl, piperazinyl or morpholinyl; and or a pharmaceutically acceptable salt thereof.

14. The method of claim 13, wherein $R^2$ is $C_{10-20}$ alkyl; and $R^6$ and $R^7$ taken together with the nitrogen to which they are attached form a 3-10 membered heterocycle that is optionally substituted with one or more groups independently selected from $C_{1-4}$ alkyl, $C_{1-4}$ haloalkyl, —F, —Cl, —Br, —I, —$OR^i$, —$SR^i$, —$N(R^i)_2$, oxo, —$NO_2$ and —CN.

15. A method of treating mitochondrial disease, neurodegenerative disease, cardiovascular disease, cancer or diabetes in an animal comprising administering to the animal an effective amount of compound of formula:

3a

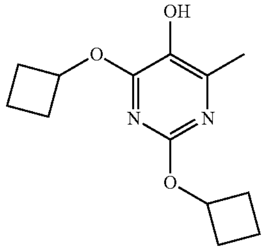

3b

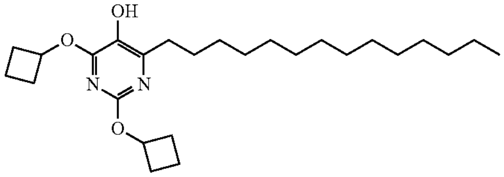

or

3c

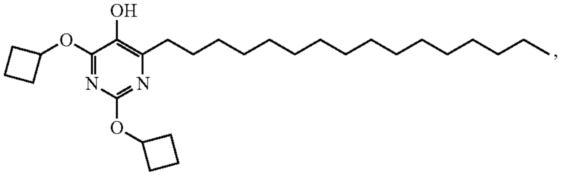

, or a pharmaceutically acceptable salt thereof.

* * * * *